(12) United States Patent
Leeflang et al.

(10) Patent No.: US 7,550,053 B2
(45) Date of Patent: Jun. 23, 2009

(54) CATHETERS WITH LUBRICIOUS LININGS AND METHODS FOR MAKING AND USING THEM

(75) Inventors: Stephen A. Leeflang, Sunnyvale, CA (US); Christian S. Eversull, Palo Alto, CA (US); Nicholas J. Mourlas, Mountain View, CA (US)

(73) Assignee: ILH, LLC, Palo Alto, CA (US)

( * ) Notice: Subject to any disclaimer, the term of this patent is extended or adjusted under 35 U.S.C. 154(b) by 242 days.

(21) Appl. No.: 11/670,958

(22) Filed: Feb. 2, 2007

(65) Prior Publication Data
US 2007/0169877 A1    Jul. 26, 2007

Related U.S. Application Data

(63) Continuation-in-part of application No. 11/340,904, filed on Jan. 26, 2006.

(60) Provisional application No. 60/764,733, filed on Feb. 2, 2006.

(51) Int. Cl.
*B32B 7/08* (2006.01)

(52) U.S. Cl. .................. 156/218; 156/515; 156/517; 156/228; 156/200; 156/201; 156/290; 156/292; 156/251; 156/256; 156/380.1; 604/523

(58) Field of Classification Search .......... 156/218, 156/515, 517, 228, 200, 201, 290, 292, 251, 156/256, 380.1; 604/523
See application file for complete search history.

(56) References Cited

U.S. PATENT DOCUMENTS 2,805,973 A * 9/1957 Klasing et al. ............... 156/251

(Continued)

FOREIGN PATENT DOCUMENTS

WO    9113648    9/1991

(Continued)

OTHER PUBLICATIONS

PCT International Search Report for PCT/US2006/039074, Applicant: ILH, LLC, Forms PCT/ISA/210 and PCT/ISA/220, dated May 23, 2007, 10 pages.

(Continued)

*Primary Examiner*—Jeff H Aftergut
*Assistant Examiner*—Jaeyun Lee
(74) *Attorney, Agent, or Firm*—William A. English; Vista IP Law Group LLP

(57) ABSTRACT

Apparatus and methods are provided for substantially continuously forming thin-walled sleeves that may be incorporated into tubular devices sized for introduction into a patient. In one embodiment, a pair of sheets including coated surfaces oriented towards one another are directed through a cutting apparatus to cut the sheets into multiple pairs of strips. The pairs of strips are bonded together to create a plurality of sleeves having lumens defined by the coated surfaces. In another embodiment, a sheet having a coated surface is fed through a cutting tool to separate the sheet into a plurality of strips, and the strips are formed into sleeves, e.g., by feeding the strips through a die or mandrel using a substantially continuous process. Optionally, the sleeves may be subsequently cut into individual tubular devices and/or further processed, e.g., by providing one or more layers around the sleeves to create catheters, sheaths, or other apparatus.

24 Claims, 25 Drawing Sheets

U.S. PATENT DOCUMENTS

| | | | |
|---|---|---|---|
| 3,269,278 A * | 8/1966 | Olstad | 493/197 |
| 3,511,435 A * | 5/1970 | Cawley et al. | 383/107 |
| 3,540,959 A * | 11/1970 | Connor | 156/203 |
| 3,879,516 A | 4/1975 | Wolvek | |
| 4,478,898 A * | 10/1984 | Kato | 428/36.91 |
| 4,516,972 A | 5/1985 | Samson | |
| 4,636,346 A * | 1/1987 | Gold et al. | 264/139 |
| 4,863,442 A | 9/1989 | DeMello et al. | |
| 5,047,045 A * | 9/1991 | Arney et al. | 606/194 |
| 5,176,661 A | 1/1993 | Evard et al. | |
| 5,217,440 A * | 6/1993 | Frassica | 604/524 |
| 5,254,107 A | 10/1993 | Soltesz | |
| 5,370,655 A | 12/1994 | Burns | |
| 5,447,497 A | 9/1995 | Sogard et al. | |
| 5,514,236 A | 5/1996 | Avellanet et al. | |
| 5,549,109 A | 8/1996 | Samson et al. | |
| 5,569,221 A * | 10/1996 | Houser et al. | 604/524 |
| 5,676,659 A | 10/1997 | McGurk | |
| 5,713,867 A | 2/1998 | Morris | |
| 5,735,809 A | 4/1998 | Gorsuch | |
| 5,811,043 A | 9/1998 | Horrigan et al. | |
| 5,836,926 A | 11/1998 | Peterson et al. | |
| 5,967,988 A | 10/1999 | Briscoe et al. | |
| 6,004,310 A | 12/1999 | Bardsley et al. | |
| 6,177,523 B1 | 1/2001 | Reich et al. | |
| 6,183,443 B1 * | 2/2001 | Kratoska et al. | 604/164.03 |
| 6,217,566 B1 * | 4/2001 | Ju et al. | 604/526 |
| 6,310,244 B1 | 10/2001 | Tran et al. | |
| 6,315,792 B1 | 11/2001 | Armstrong et al. | |
| 6,511,462 B1 | 1/2003 | Itou et al. | |
| 6,592,576 B2 | 7/2003 | Andrews et al. | |
| 6,669,886 B1 | 12/2003 | Willard | |
| 6,830,568 B1 | 12/2004 | Kresten et al. | |
| 6,837,890 B1 | 1/2005 | Chludzinski et al. | |
| 6,942,654 B1 | 9/2005 | Schaefer et al. | |
| 6,945,970 B2 | 9/2005 | Pepin | |
| 6,946,173 B2 | 9/2005 | Lim et al. | |
| 6,979,290 B2 | 12/2005 | Mourlas | |
| 7,188,623 B2 | 3/2007 | Anderson et al. | |
| 7,273,469 B1 | 9/2007 | Chan et al. | |
| 7,306,585 B2 * | 12/2007 | Ross | 604/523 |
| 2001/0016702 A1 * | 8/2001 | Benjamin | 604/19 |
| 2001/0053931 A1 * | 12/2001 | Hess et al. | 623/1.15 |
| 2002/0156494 A1 | 10/2002 | Simhambhatla et al. | |
| 2003/0233115 A1 | 12/2003 | Eversull et al. | |
| 2004/0097788 A1 | 5/2004 | Mourlas et al. | |
| 2005/0085841 A1 | 4/2005 | Eversull et al. | |
| 2005/0085842 A1 | 4/2005 | Eversull et al. | |
| 2005/0149104 A1 | 7/2005 | Leeflang et al. | |
| 2005/0197623 A1 | 9/2005 | Leeflang et al. | |
| 2005/0228452 A1 | 10/2005 | Mourlas et al. | |
| 2007/0074805 A1 | 4/2007 | Leeflang et al. | |
| 2007/0075452 A1 | 4/2007 | Leeflang | |
| 2007/0088296 A1 | 4/2007 | Leeflang | |

FOREIGN PATENT DOCUMENTS

| | | |
|---|---|---|
| WO | 9620750 | 7/1996 |
| WO | 9740880 | 11/1997 |
| WO | 9851370 | 11/1998 |
| WO | 9937350 | 7/1999 |
| WO | 0107101 | 2/2001 |
| WO | 03/020353 | 3/2003 |
| WO | 2004075961 | 9/2004 |

OTHER PUBLICATIONS

PCT Written Opinion for PCT/US2006/039074, Applicant: ILH, LLC, Forms PCT/ISA/237, dated May 23, 2007, 13 pages.

Office Action for U.S. Appl. No. 11/340,904, May 14, 2008, 23 pages.

William A. English, Attorney for Applicant, Response to Office Action for U.S. Appl. No. 11/340,904, May 14, 2008, 19 pages.

Office Action for U.S. Appl. No. 11/341,324, May 28, 2008, 13 pages.

William A. English, Attorney for Applicant, Response to Office Action for U.S. Appl. No. 11/341,324, Oct. 28, 2008, 15 pages.

Office Action for U.S. Appl. No. 11/340,944, Sep. 30, 2008, 10 pages.

* cited by examiner

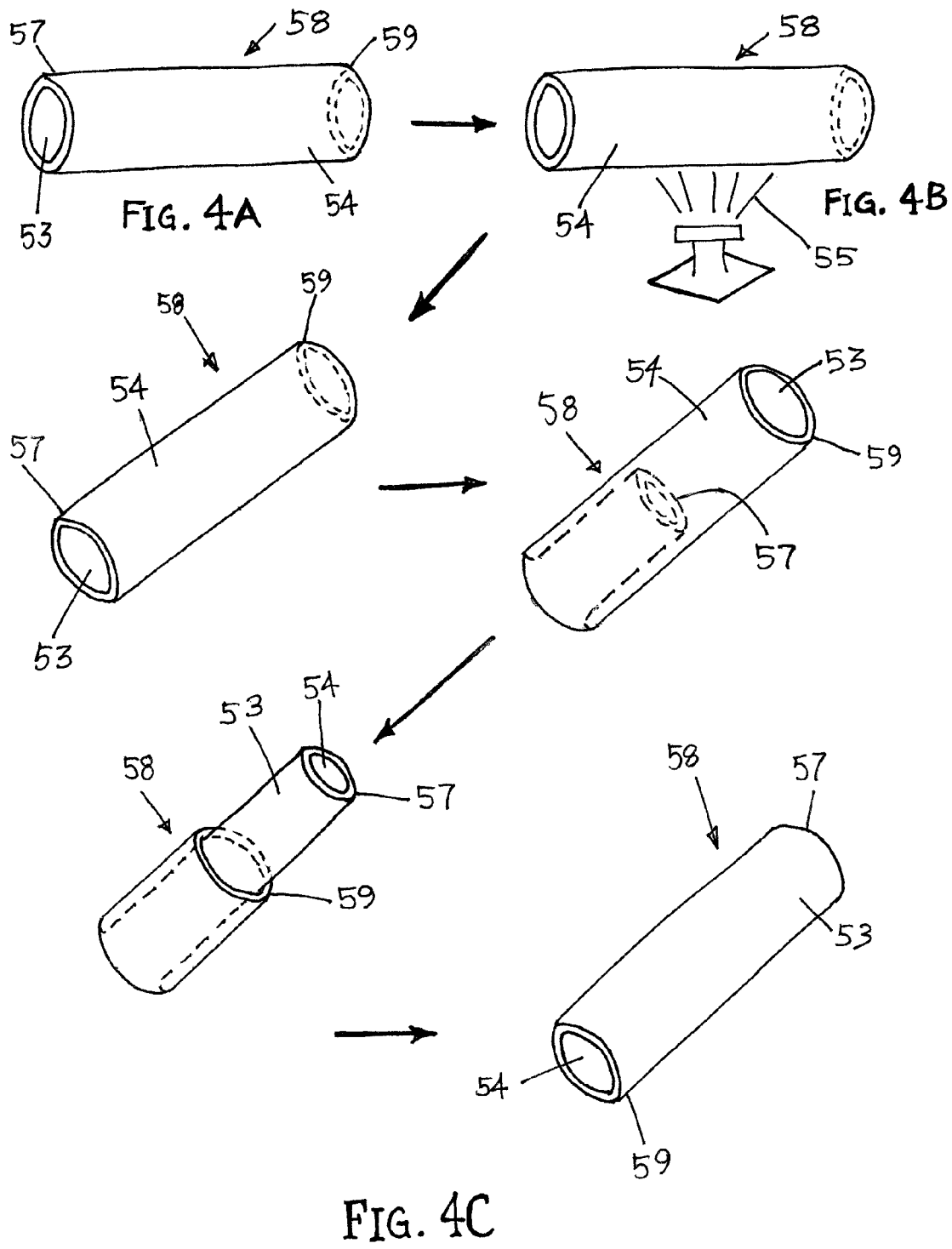

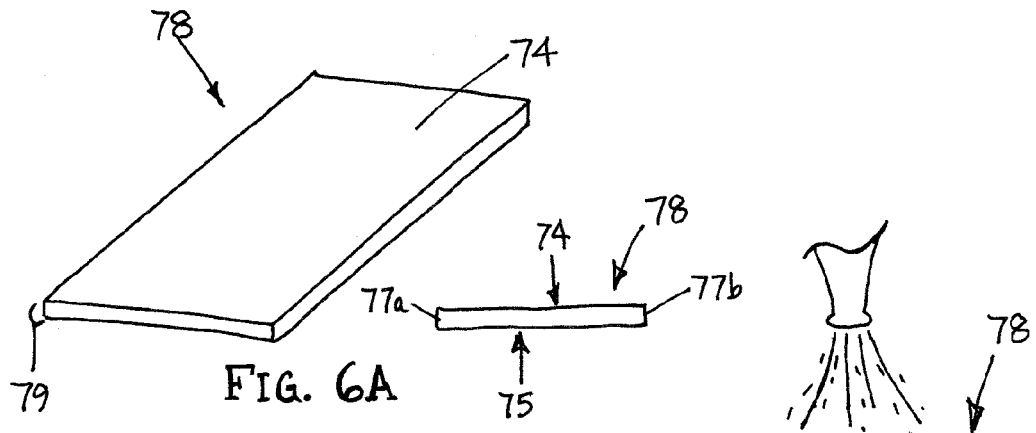
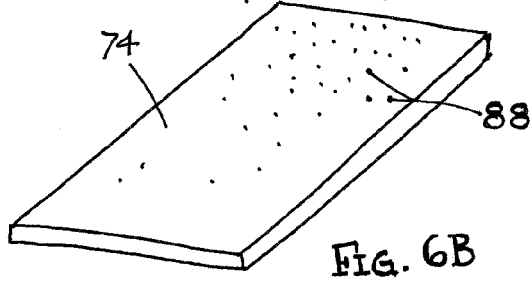
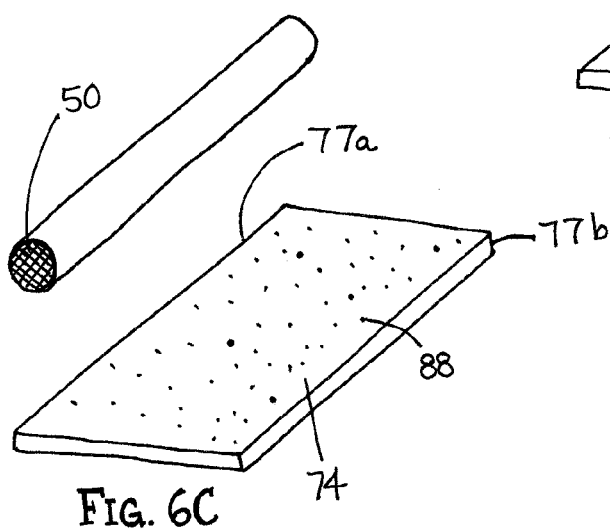
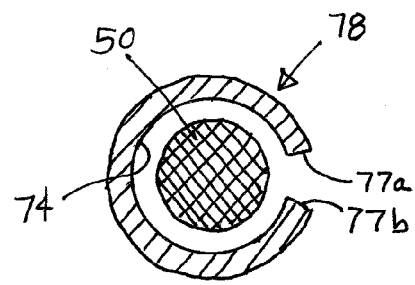
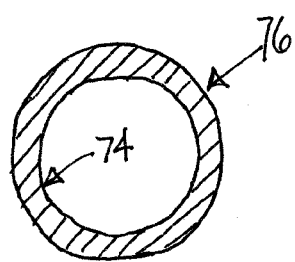

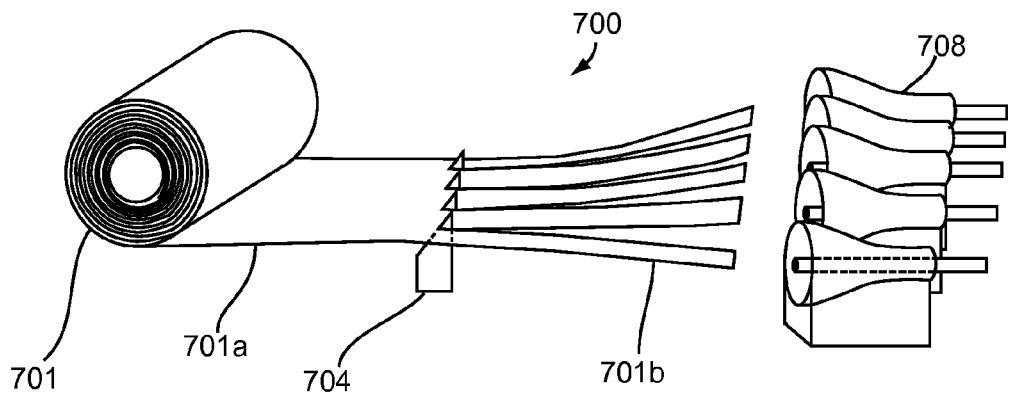
FIG. 15A
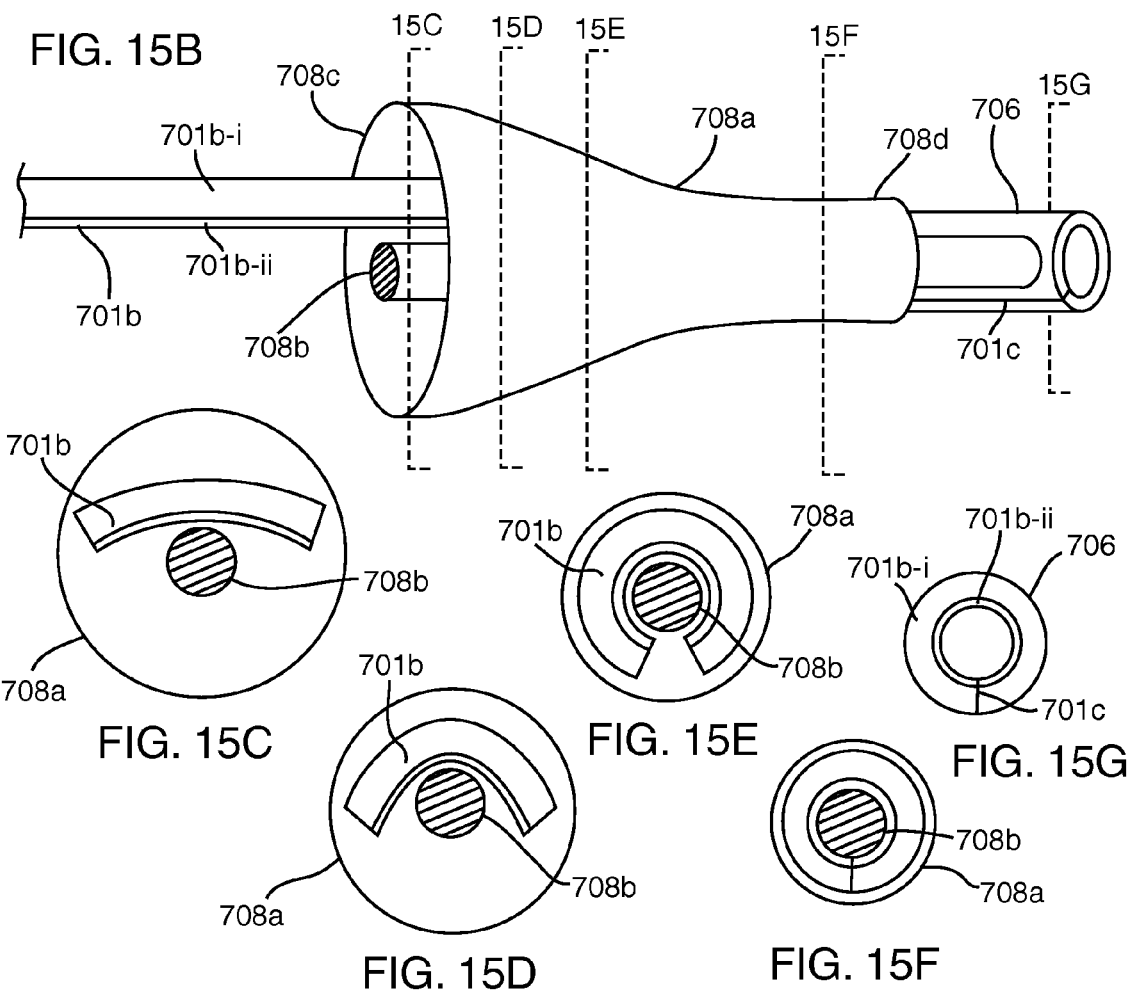
FIG. 15B
FIG. 15C
FIG. 15D
FIG. 15E
FIG. 15F
FIG. 15G

CATHETERS WITH LUBRICIOUS LININGS AND METHODS FOR MAKING AND USING THEM

This application claims benefit of provisional application Ser. No. 60/764,733, filed Feb. 2, 2006, and is a continuation-in-part of co-pending application Ser. No. 11/340,904, filed Jan. 26, 2006, the entire disclosures of which are expressly incorporated herein by reference.

FIELD OF THE INVENTION

The present invention relates generally to devices for providing access into body lumens and, more particularly, to catheters, sheaths, and other tubular devices with lubricious linings and methods for making and using them.

BACKGROUND

Catheters are elongate tubular devices sized for introduction into body passages and cavities of a patient, such as a patient's vascular system, gastrointestinal system, abdominal cavity, and the like. A catheter may include one or more lumens intended for passing various other devices, agents, and/or fluids into a body lumen or cavity accessed by the catheter. For such applications, the properties of the inner surface of one or more lumens of the catheter may significantly impact the performance of the catheter. In particular, the lubricity of the inner surface may affect the ability to pass other devices, agents, and/or fluids through the lumen(s) of the catheter.

To enhance lubricity, it has been suggested to include polytetraflouroethylene ("PTFE"), polyethylene ("PE") or other cores surrounding the lumen of a catheter. The inner core may be intended to provide a lubricious inner surface to facilitate passing guidewires, pacing leads, or other devices through the lumen of the catheter. Constructing such a catheter, however, is complicated because of the difficulty bonding the inner core to the outer portions of the catheter.

For example, PTFE, in its native form is nearly impossible to bond; consequently, it must be held in place by mechanical interaction or must be etched in order to impart bondability. Further, because of the inaccessibility of the inner surface of the lumen of a catheter, mechanical abrasion or modification, cleaning, etching, application of adhesive, or other modifications of the inner surfaces to facilitate bonding are generally difficult to complete. Furthermore, materials such as PTFE may degrade under commonly used sterilization techniques, such as gamma sterilization, and therefore may be inappropriate for certain catheter devices. PE, similar to PTFE, is also difficult to bond to other materials. In some cases, a third material must be used that is bondable both to PE and to other plastics. In both cases, the manufacturing process is complicated and the materials generally expensive.

Other methods for imparting lubricity to inner surfaces have been tried, for example, vapor deposition of surface coatings such as Paralene; however, this process is also complicated and does not result in optimal lubricity.

Hydrophilic coatings are well known and are widely used in medical devices. These are readily applied to outer surfaces and frequently used on exteriors of catheters, for example, to facilitate tracking through the vasculature. However, application of such coatings to inner surfaces is currently significantly hindered by technical challenges and therefore not practiced generally.

Hydrophilic coatings are generally dispersed within a solvent, for example, an aqueous or alcohol based solvent, which is applied to a surface and spread evenly in order to deposit a substantially uniform layer of dissolved hydrophilic coating on the surface after evaporation of the solvent. Given the appropriate processing equipment, techniques for coating exterior surfaces of catheters are known. Generally, this is accomplished by dipping. However, inner surfaces, especially small lumens of long catheters, are extremely difficult or impossible to coat because of the difficulty of evenly applying a solution to the inner surface.

For example, the size and geometry of an inner surface, e.g., a small round inner diameter of a catheter, may cause the solution to readily bead up rather than disperse evenly over the surface. Even if the solution could be evenly dispersed over the surface, for example, by addition of surfactants, evaporation of a solvent from inside a long small diameter tube may be slow and irregular, with condensation likely along the way. Thus, this method of coating an inner surface may not be feasible.

Furthermore, once the hydrophilic coating has been evenly deposited, it is often desirable to cross-link or otherwise increase the strength of adhesion of the coating, e.g., using heat or ultraviolet ("UV") light. In the case of UV light, it may be difficult to expose an inner surface of a catheter to UV light in order to cross-link the coating, unless the material being coated were transparent to UV light. Excessive exposure to UV light may also cause material degradation. Application of heat likewise is not always practicable as it may damage other device components.

With respect to coating outer surfaces, current methods make it relatively difficult to coat discrete sections without masking. Furthermore, the equipment and fixtures required for coating are generally expensive and processes may be difficult to control.

Due to these challenges, surface modification of inner surfaces, as for example, by application of hydrophilic, anti-anti-thrombotic, anti-biotic, drug-eluting, or other coatings is not easily accomplished, although it would be useful in a variety of applications. Furthermore, while coating outer surfaces is often performed, various limitations exist in current processes, which may be improved upon.

SUMMARY OF THE INVENTION

The present invention is directed generally to apparatus and methods for providing access to body lumens and/or for delivering instruments and/or agents into body lumens during a medical procedure. For example, in some embodiments, simple and/or readily practicable methods are provided for making tubular devices having coated inner and/or outer surfaces. As a further example, in some embodiments, simple and/or readily practicable methods are provided for creating a sleeve having coated inner and/or outer surfaces. Furthermore, methods are provided for coating sheets in a readily coatable configuration and forming them into various useful configurations while preserving the surface properties imparted by the coating. Furthermore, several devices are disclosed including coated inner and/or outer surfaces that provide one or more desired properties to the coated surfaces.

In accordance with one embodiment, a method is provided for making a tubular device. A thin sheet is coated on a first surface with a coating having one or more desired properties, e.g., a hydrophilic material having a predetermined lubricity. The sheet is rolled such that first and second side edges of the sheet are disposed adjacent one another and the coating is disposed inwardly. A longitudinal seam is created along the first and second side edge to create a sleeve.

A tubular structure is attached around the sleeve to create a tubular device. The sleeve and tubular structure may be attached together by at least one of laminating, bonding, and heat sealing. The tubular structure is generally attached in such a way as to substantially maintain the properties of the coated surface.

In an exemplary embodiment, the sleeve is positioned around a mandrel to create a first assembly, and the tubular structure is positioned over the first assembly to create a second assembly. Heat shrink tubing may be positioned over the second assembly, and heated to heat and/or compress the tubular structure. For example, the tubular structure may be heated sufficiently to cause the tubular structure to at least partially reflow to bond or laminate the tubular structure around the sleeve. After sufficient heating, the shrink tubing may be removed from around the second assembly, and the mandrel removed to create the tubular device. Alternatively, the tubular structure, thin sheet, and mandrel may be directed through a heated die to attach the tubular structure to the thin sheet.

In accordance with another embodiment, a method is provided for making a tubular device that includes coating a first surface of a thin sheet with a coating imparting one or more desired properties to the first surface. The thin sheet may be wrapped at least partially around a mandrel with the first surface disposed inwardly. A slotted tube may be positioned around the thin sheet and mandrel, and attached to the thin sheet to form a tubular structure.

In an exemplary embodiment, the thin sheet is wrapped only partially around the mandrel such that excess edges of the thin sheet are disposed adjacent one another away from the mandrel. After the slotted tube is attached to the thin sheet, excess edges of the thin sheet may be trimmed from the tubular structure.

In another embodiment, the slotted tube includes longitudinal edges defining a slot, and the slotted tube may be positioned around the thin sheet and mandrel by separating the longitudinal edges. The longitudinal edges may be bonded together when the slotted tube is attached to the thin sheet, e.g., by reflowing or otherwise heating material of the slotted tube.

In accordance with yet another embodiment, a method is provided for making a tubular device sized for introduction into a body lumen that includes providing a sheet of material comprising a first surface and a second surface, coating the first surface of the sheet with a coating, rolling the sheet until longitudinal edges of the sheet are disposed adjacent one another, and attaching the longitudinal edges to one another to form a continuous wall defining a lumen.

In exemplary embodiments, the longitudinal edges may be attached to one another by using at least one of heat bonding, an adhesive, and/or lamination.

In accordance with still another embodiment, a tubular device is provided that includes a proximal end, a distal end sized for introduction into a body lumen, and a lumen extending between the proximal and distal ends. In one embodiment, the tubular device may include an inner polyurethane liner including a coating on an inner surface thereof, and an outer layer, e.g., including PEBAX, nylon, and/or urethane. For example, the tubular device may be a delivery sheath, which may include a braid surrounding at least a portion of the liner. In another example, the tubular device may be a core for a guidewire lumen. In yet another example, the polyurethane liner may be Ether-based or Esther-based, the latter of which may improve cross linking and/or adhesion of the coating.

In accordance with yet another embodiment, a lead is provided that includes a proximal end, a distal end sized for introduction into a body lumen and at least one electrode on the distal end. The lead may include a lead body having an outer surface extending between the proximal and distal ends, and a polyurethane cover surrounding at least a portion of the outer surface. The cover may include a coating imparting one or more predetermined properties to the portion of the outer surface, e.g., including a lubricious and/or hydrophilic material. Optionally, the cover may be removable from around the lead body.

In accordance with still another embodiment, a method is provided for making a plurality of tubular devices sized for introduction into a body lumen. Initially, first and second sheets may be provided adjacent one another such that first surfaces of the sheets are oriented towards one another and second surfaces of the sheets are oriented away from one another. The first and second sheets may be directed through a cutting apparatus such that the first and second sheets are cut into multiple pairs of strips, and the pairs of strips may be bonded together to create a plurality of thin-walled sleeves having inner lumens defined by the first surfaces.

In an exemplary embodiment, the sheets may be fed substantially continuously through the cutting apparatus such that long thin-walled sleeves may be created that may be subsequently cut or otherwise separated into individual tubular devices. Optionally, the sleeves may be subsequently processed, e.g., by providing one or more layers around the sleeves to create catheters, sheaths, or other apparatus.

In accordance with yet another embodiment, a method is provided for making a plurality of tubular devices sized for introduction into a body lumen that includes providing first and second sheets adjacent one another such that first surfaces of the sheets are oriented towards one another and second surfaces of the sheets are oriented away from one another, the first surfaces comprising a coating having one or more desired properties; directing the first and second sheets through a cutting apparatus to cut the first and second sheets into multiple pairs of strips defining longitudinal edges and bonding the longitudinal edges of adjacent first and second strips to create a plurality of thin-walled sleeves having inner lumens defined by the first surfaces; and cutting each of the thin-walled sleeves into a plurality tubular devices.

In accordance with still another embodiment, a method is provided for making a plurality of tubular devices sized for introduction into a body lumen that includes providing a first sheet having first and second surfaces, the first surface comprise a coating having one or more desired properties; feeding the first sheet through a cutting tool to separate the first sheet into a plurality of elongate strips; and forming the strips into elongate sleeves such that the first surface defines a lumen within the sleeves. Optionally, each of the sleeves may be cut into individual tubular devices and/or further processed, e.g., to provide one or more outer layers, and the like.

In accordance with yet another embodiment, a method is provided for making a tubular device sized for introduction into a body lumen that includes providing a sheet of material comprising a first surface and a second surface, coating the first surface of the sheet with a coating, rolling the sheet at least partially around a mandrel until longitudinal edges of the sheet are disposed near or adjacent one another to create a first assembly. A tubular structure and/or other outer layer may be positioned over the first assembly to create a second assembly. Optionally, heat shrink tubing may be positioned over the second assembly, and heated to heat and/or compress the tubular structure. For example, the tubular structure may be heated sufficiently to cause the tubular structure to at least partially reflow to bond or laminate the tubular structure to the sheet. After sufficient heating, the shrink tubing may be removed from around the second assembly, and the mandrel removed to create the tubular device.

In still another embodiment, a method is provided for making a tubular device sized for introduction into a body lumen that includes providing a sheet of material comprising a first surface and a second surface, coating the first surface of the sheet with a coating, rolling the sheet at least partially around a mandrel until longitudinal edges of the sheet are disposed near or adjacent one another to create a first assembly. A braid may be positioned over the first assembly to create a second assembly. A tubular structure may be positioned over the second assembly to create a third assembly. Heat shrink tubing may be positioned over the third assembly, and heated to heat and/or compress the tubular structure. For example, the tubular structure may be heated sufficiently to cause the tubular structure to at least partially reflow to bond or laminate the tubular structure to the sheet. After sufficient heating, the shrink tubing may be removed from around the third assembly, and the mandrel removed to create the tubular device.

Other aspects and features of the present invention will become apparent from consideration of the following description taken in conjunction with the accompanying drawings.

BRIEF DESCRIPTION OF THE DRAWINGS

FIGS. 2A and 2B are perspective views of a thin film sheet being coated, and FIGS. 2C and 2D are perspective views showing the coated sheet being rolled to create the thin-walled sleeve.

FIGS. 4A-4C are perspective views, showing a method for coating and inverting a thin-walled sleeve.

FIGS. 6A-6C are perspective views and FIGS. 6D and 6E are cross-sectional views, showing yet another method for making a tubular device including a coated inner surface.

FIG. 15A is a side view of another embodiment, showing an apparatus and method for making multiple thin-walled sleeves substantially simultaneously.

FIG. 15B is a detail of an exemplary die of the apparatus of FIG. 15A, for forming thin sheets into thin-walled sleeves.

FIGS. 15C-15G are cross-sections of the die of FIG. 15B, showing the orientation of an exemplary thin sheet as it passes through the die.

DETAILED DESCRIPTION

Figure 1A:
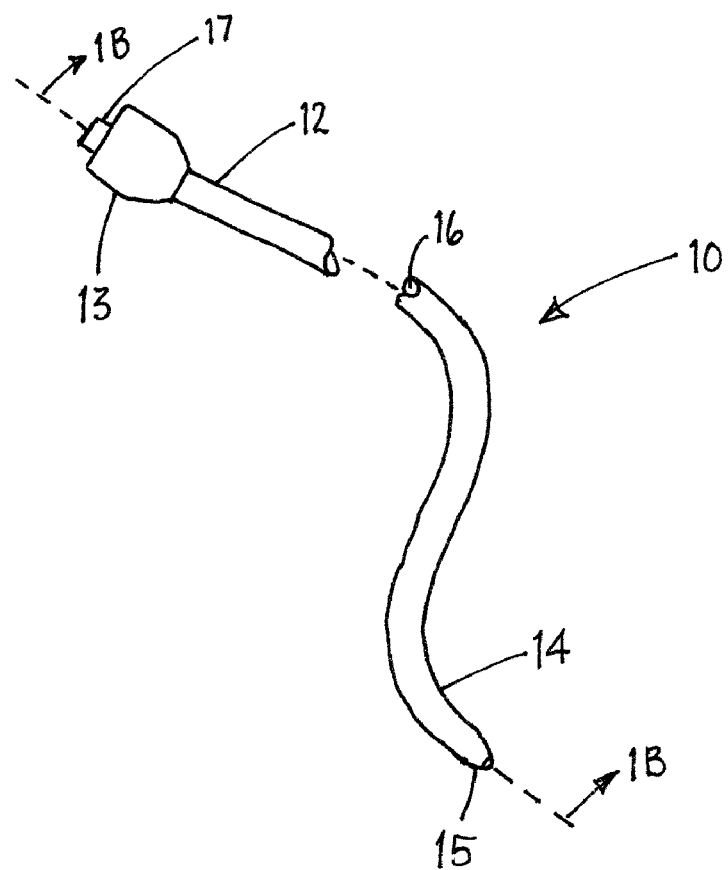
FIG. 1A is a perspective view of an exemplary embodiment of a tubular device, including a lumen extending between proximal and distal ends thereof.
Figure 1B:
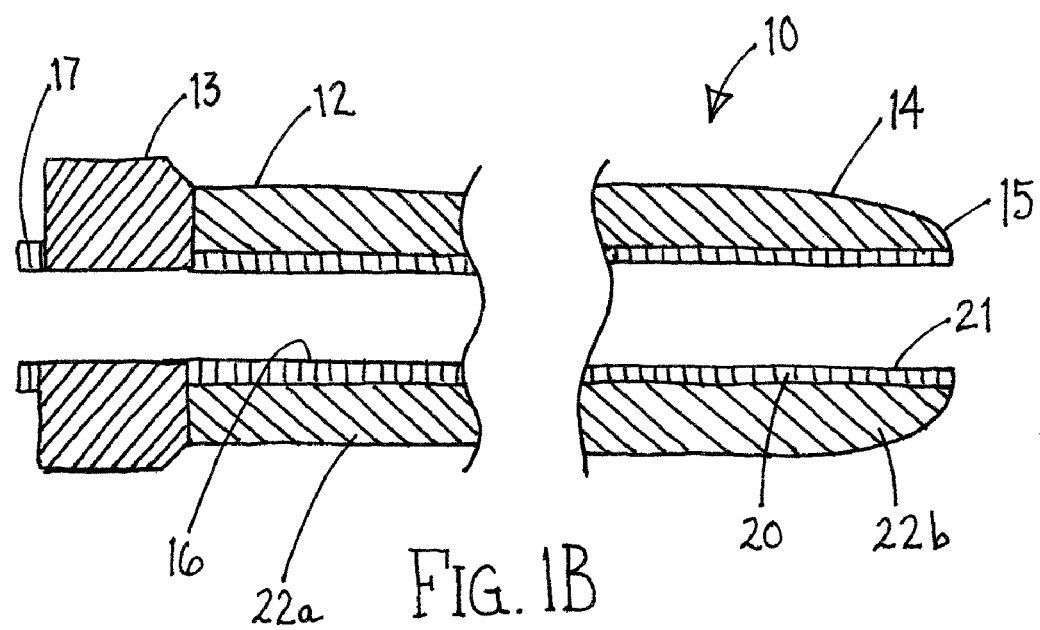
FIG. 1B is a cross-sectional view of the tubular device of FIG. 1A, taken along line 1B-1B, showing a coated liner surrounding the lumen and an outer layer surrounding the coated liner.

Turning to the drawings, FIGS. 1A and 1B show an exemplary embodiment of an apparatus 10 for accessing a body lumen (not shown) and/or for delivering one or more fluids, agents, and/or instruments (also not shown) within a body lumen. In exemplary embodiments, the apparatus 10 may be a guide catheter, a procedure catheter, a sheath, an imaging device, or other tubular device sized for introduction into a body lumen, such as a vessel within a patient's vasculature, a passage within a patient's gastrointestinal tract, urogenital tract, reproductive tract, respiratory tract, lymphatic system, and the like, as described further below.

Generally, the apparatus 10 is an elongate tubular member including a proximal end 12, a distal end 14 sized for insertion into a body lumen, and a lumen 16 extending between the proximal and distal ends 12, 14. Optionally, the apparatus 10 may include one or more additional lumens (not shown), which may be disposed concentrically around or side-by-side with the lumen 16. The lumen 16 may be sized for receiving a guide wire, procedure catheter, cardiac lead, needle, or other instrument (not shown), and/or for delivering fluids or other flowable agents or materials therethrough.

Optionally, the distal end 14 may include a tapered, rounded, or otherwise shaped distal tip 15, e.g., to provide a substantially atraumatic tip and/or facilitate advancement or navigation through various anatomy. In addition or alternatively, the distal end 14 may include one or more therapeutic and/or diagnostic elements, e.g., one or more balloons, stents, sensors, electrodes, steering mechanisms, imaging devices, needles, and the like (not shown), depending upon the particular intended application for the apparatus 10.

Optionally, the proximal end 12 may include a handle 13 and/or one or more ports, e.g., port 17 communicating with the lumen 16. In addition or alternatively, the handle 13 and/or proximal end 12 may include one or more connectors, such as luer lock connectors, electrical connectors, and the like, for connecting other devices (not shown) to the apparatus 10, such as syringes, displays, controllers, and the like (also not shown). In addition, the handle 13 may include one or more actuators, such as sliders, buttons, switches, and the like, e.g., for activating and/or manipulating components (also not shown) on the distal end 14 or otherwise operating the apparatus 10.

With particular reference to FIG. 1B, the apparatus 10 generally includes an inner liner 20 surrounding the lumen 16 and an outer layer 22 surrounding the inner liner 20. The inner liner 20 may include a relatively thin film, sheet, or other material including an inner surface 21. The inner surface 21 may include a coating having one or more desired properties, e.g., a predetermined lubricity, hydrophilic characteristic, and the like. The outer layer 22 may be attached to the inner layer 20, e.g., by laminating, adhering, adhesive bonding, ultrasonic welding, reflowing or other heating, and the like, as described elsewhere herein.

Optionally, the outer layer 22 may include one or more sublayers (not shown). For example, the outer layer 22 may include a braided or helical reinforcing layer (not shown) surrounding the inner layer 20 and one or more tubular layers (also not shown) surrounding the reinforcing layer and/or between the reinforcing layer and the inner layer 20. In exemplary embodiments, the reinforcing layer may include one or more round or flat wires, filaments, strands, and the like, e.g., formed from metal, such as stainless steel, plastic, woven fibers, such as glass, Kevlar, and the like, or composite materials. Materials that may be used in the outer layer 22 include PEBAX, urethane, FEP, PFA, polyethylene ("PE"), polyamide (Nylon), silicone, polypropylene, polysulfone, polyvinylchloride (PVC), polystyrene, polycarbonate, polymethylmethacrylate, and the like. Materials may be primarily selected for optimal mechanical, bonding, and/or other properties and subsequently imparted with desired surface properties, for example lubricity, by coating.

Exemplary outer layers that may be included in the apparatus 10 and methods for making them are disclosed in U.S. Pat. Nos. 4,478,898, 4,863,442, 5,217,440, 5,254,107, 5,676, 659, 5,811,043, 5,836,926, 6,004,310, 6,669,886, 6,837,890, and 6,945,970. The entire disclosures of these references are expressly incorporated by reference herein.

The outer layer 22 may have a substantially homogenous construction between the proximal and distal ends 12, 14. Alternatively, the construction may vary along the length of the apparatus 10 to provide desired properties. For example, the outer layer 22a at or adjacent the proximal end 12 may be substantially rigid or semi-rigid, e.g., providing sufficient column strength to allow the apparatus 10 to be pushed from the proximal end 12. In addition, the reinforcing layer or other material in the outer layer 22 may allow the apparatus 10 to be twisted from the proximal end 12, e.g., to rotate the distal end 14 within a patient's body. Thus, the distal end 14 of the apparatus 10 may be manipulated within a patient's body from the proximal end 12 without substantial risk of buckling and/or kinking. Optionally, the outer layer 22b at or adjacent the distal end 14 may be substantially flexible or semi-rigid, e.g., to allow the distal end 14 to bend easily or otherwise be advanced through tortuous anatomy and/or provide a substantially atraumatic distal tip 15. Furthermore, the outer layer 22a, may have one or more transition regions along its length, transitioning from one desired construction to another.

In exemplary embodiments, the apparatus 10 may have an outer diameter between about half and twenty millimeters (0.5-20 mm), and a length between about five and one hundred fifty centimeters (5-150 cm). The inner liner 20 may have a wall thickness between about 0.0001-0.01 inch (0.0025-0.25 mm) and the outer layer 22 may have a wall thickness between about 0.0005-0.2 inch (0.0127-5.08 mm).

Figure 2A:
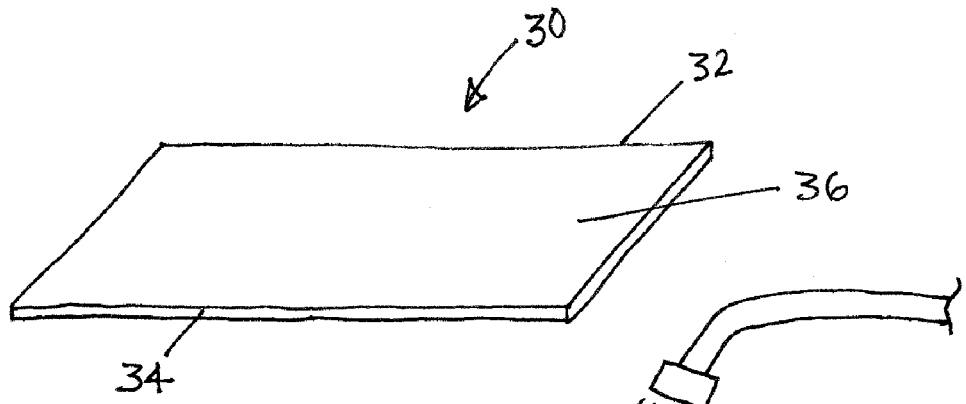
FIGS. 2A-2D show a first method for making a thin-walled sleeve.
Figure 2B:
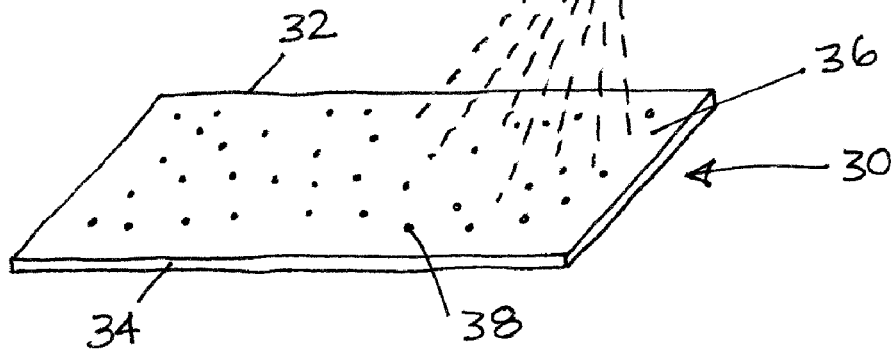

Turning to FIGS. 2A-2D and 3A-3E, a first exemplary method is shown for making a tubular device, such as apparatus 10 described above. Initially, as shown in FIG. 2A, a thin film sheet 30 may be provided including a first side edge 32 and a second side edge 34 opposite one another, and a first upper surface 36 and a second lower surface (not shown). The sheet 30 may be formed from a single layer or multiple layers of material. In an exemplary embodiment, the sheet 30 may be formed from a sheet of polyurethane, e.g., having a thickness between about 0.0001-0.01 inch (0.0025-0.25 mm). For example, the polyurethane may be Ether-based or Ester-based. However, other suitable polymers may also be used, such as polyolefin, PEBAX, nylon, silicone, polypropylene, and polyethylene.

With the sheet 30 substantially flat, a coating 38 is applied to the first surface 36. Alternatively, the sheet 30 may be disposed in a concave, convex, or other nonplanar configuration (not shown), as long as the first surface 36 is readily accessible. In an exemplary embodiment, the coating includes a hydrophilic material, such as Polyvinylpyrrolidone, and is sprayed onto the first surface 36 to apply a substantially uniform thickness coating.

Alternatively, the coating may be applied using other procedures, such as rolling, brushing, spreading by maer rods, or dipping, e.g., to provide a substantially uniform thickness coating 38 on the first surface 36. The hydrophilic material may provide a predetermined lubricity on the first surface 36. Alternatively, other materials may be applied to provide one or more desired properties on the first surface 36, e.g. anti-thrombotic or anti-hemolytic materials, drug-eluting coatings, and the like.

Figure 2C:
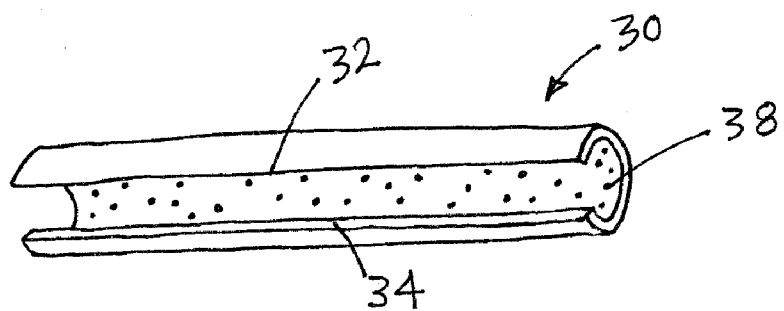

Turning to FIG. 2C, the sheet 30 may be rolled such that the first and second side edges 32, 34 are disposed adjacent one another and the first upper surface 36 is now disposed inwardly. The first and second side edges 32, 34 may then be attached to one another to create a relatively thin-walled sleeve 40.

Figure 2D:
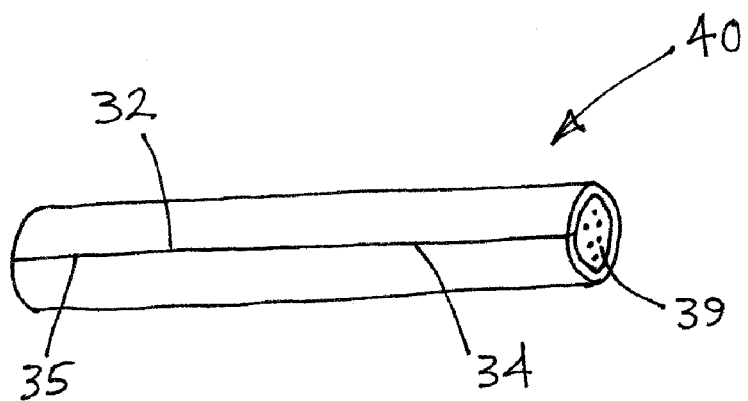

In an exemplary embodiment, the side edges 32, 34 may be lapped against one another along the uncoated surface or the side edges 32, 34 may be butted against one another. The side edges 32, 34 may then be attached to one another to create a longitudinal seam 35, as shown in FIG. 2D. Optionally, the sheet 30 may be wrapped around a mandrel (not shown), which may facilitate attaching the side edges 32, 34 and/or facilitate maintaining a desired inner diameter for the sleeve 40.

In these configurations, the coating 38 may not interfere with attaching the side edges 32, 34 together, because the contact surface between the side edges 32, 34 is uncoated. In exemplary embodiments, the side edges 32, 34 are attached to one another by heat bonding, i.e., heating to fuse the side edges 32, 34 together, using ultrasonic energy, and/or using one or more adhesives. The resulting device is a relatively thin-walled sleeve 40 including a lumen 39 having an inner surface coated, as shown in FIG. 2D. Optionally, if any excess material remains between the side edges 32, 34 and the longitudinal seam, the excess material may be cut away or otherwise removed from the thin-walled sleeve 40.

Turning to FIGS. 3A-3E, the thin-walled sleeve 40 may be incorporated into a catheter or other tubular device, similar to the apparatus 10 described above. It will be noted that annular spaces are shown between the various layers or components shown in the drawings. These spaces are not to scale but are shown merely to clarify the various components. It will be appreciated that the spaces may be relatively small or adjacent components may directly contact one another such that there is little or substantially no space between the contacting components or layers.

Figure 3A:
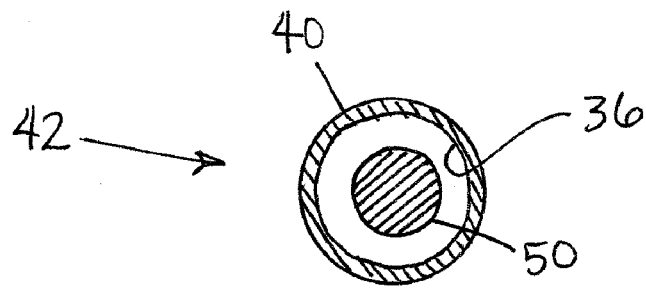
FIGS. 3A-3E are cross-sectional views, showing a method for making a tubular device including a thin-walled sleeve.

For example, as shown in FIG. 3A, the thin-walled sleeve 40 may be positioned around a mandrel 50, thus creating a first assembly 42. The mandrel 50 may be an elongate cylindrical structure, e.g., a tube or rod, formed from material able to withstand the parameters used during assembly, e.g., elevated temperatures used to heat the materials during assembly. The thin-walled sleeve 40 may fit relatively snugly around the mandrel 50 such that the inner surface 36 is substantially smooth, e.g., without substantial wrinkles or other irregularities.

The mandrel 50 may be formed from or coated with a lubricious, hydrophilic, or other material that is non-bondable to the thin-walled sleeve 40. Exemplary materials for the mandrel 50 may include metal, such as stainless steel, coated stainless steel, NiTi alloy, MP35N, Elgiloy, and the like. Alternatively or in addition, plastic, such as Teflon, composite, or non-metallic materials may be used.

Figure 3B:
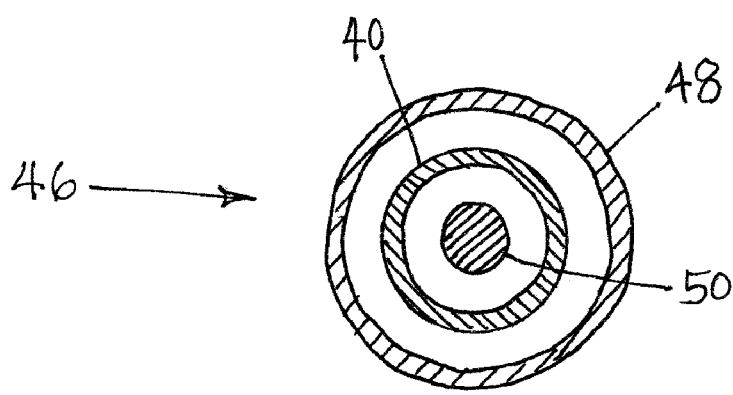

Turning to FIG. 3B, a tubular structure 48 is then positioned over the first assembly 42, creating a second assembly 46. In an exemplary embodiment, the tubular structure 48 may be an extrusion of PEBAX, nylon, polyimide, HDPE, Plexar, and/or Urethane having an inner diameter sized to slide around the thin-walled sleeve 40. Alternatively, other suitable materials described herein may also be employed, such as the multiple sublayer outer layers described above.

Generally, the tubular structure 48 may have a thickness that is substantially greater than a thickness of the thin-walled sleeve 40. Thus, the tubular structure 48 may provide the desired structural integrity of the final apparatus being constructed. Nevertheless, the material of the thin-walled sleeve may also be selected based on desired mechanical or structural properties and desired surface properties subsequently imparted by coating. In exemplary embodiments, the tubular structure 48 may be extruded or otherwise flowed around the thin-walled sleeve 40, or may be preformed and then threaded or otherwise advanced over the thin-walled sleeve 40. Alternatively, the tubular structure 48 may be built up around the thin-walled sleeve 40, e.g., by applying one or more successive layers around the thin-walled sleeve 40 until a desired outer layer is obtained.

Figure 3C:
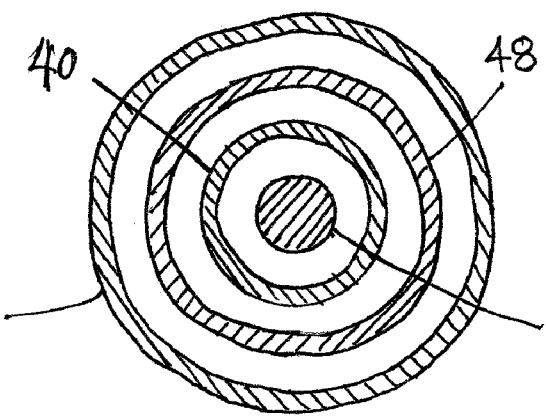

Turning to FIG. 3C, heat shrink tubing 45 may be positioned over the second assembly 46, and then heat may be applied to the heat shrink tubing 45, e.g., sufficient to cause the shrink tubing 45 to shrink around the second assembly 46. The combination of heat and inward compression may cause the tubular structure 48 to at least partially melt or otherwise reflow around the thin-walled sleeve 40, thereby fusing the tubular structure 48 to the thin-walled sleeve 40. For example, hot air may be blown around the shrink tubing 45 or the entire assembly may be placed in an oven, creating sufficient heat to cause the shrink tubing 45 to constrict around the tubular structure 48.

Figures 3D, 3E:
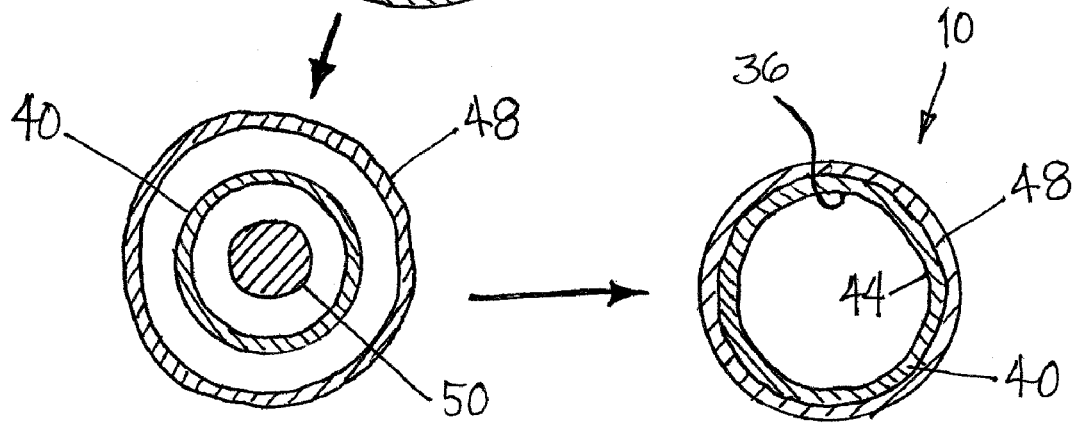

As shown in FIG. 3D, the shrink tubing 45 may then be removed from the second assembly 46. For example, the shrink tubing 45 may be formed from a material that may be torn easily. In addition or alternatively, the shrink tubing 45 may include one or more weakened seams, tabs, and the like (not shown) to facilitate removing the shrink tubing from around the second assembly 46. Alternatively, the shrink tubing 45 may be rolled, slid, or otherwise removed from one end of the tubular structure 48. As seen in FIG. 3E, the mandrel 50 may be removed from within the thin-walled sleeve 40 either before or after removing the shrink tubing 45.

The result is a tubular device that includes an outer layer 48, and a lumen 44 including a coated inner surface. Optionally, one or more additional components may be added to the tubular device, such as a handle and/or one or more therapeutic and/or diagnostic elements, as described above.

Figure 4D:
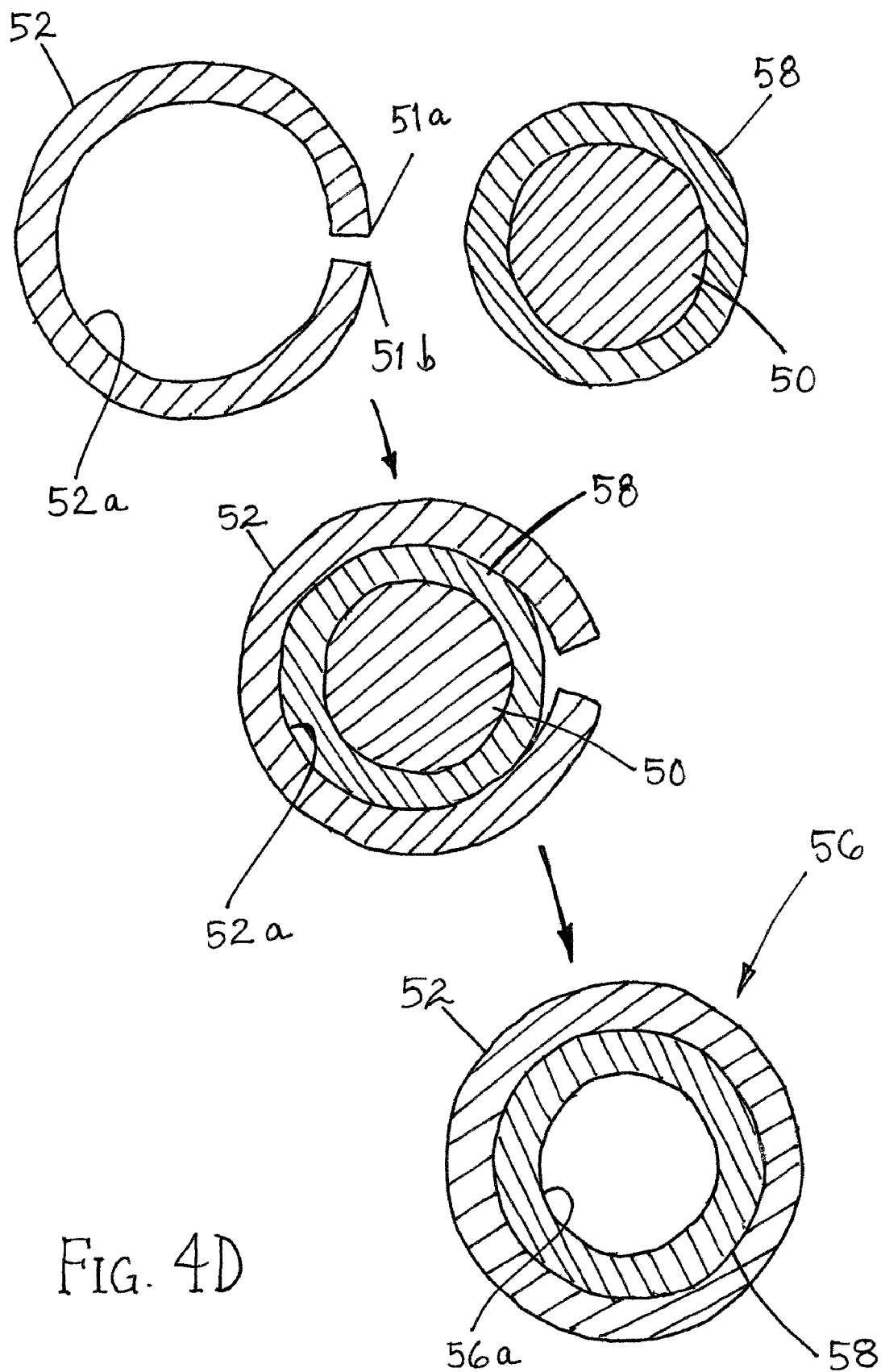
FIG. 4D is a cross-sectional view and FIGS. 4E-4G are perspective views, showing a method for making a tubular device including a thin-walled sleeve.

Turning to FIGS. 4A-4G, another method is shown for making a tubular device, such as apparatus 10 described above. As shown in FIG. 4A, a relatively thin-walled sleeve 58 may be provided that initially includes first and second ends 57, 59 defining an outer surface 54 and an inner surface 53 extending therebetween. The thin-walled sleeve 58 may include a tube of thin-walled material including one or more layers, similar to the sheet described above. The thin-walled sleeve 58 may be formed from continuous extrusion, injection molding, blow molding, and the like. Alternatively, the sleeve 58 may be formed from a sheet that is rolled and has its longitudinal edges sealed or otherwise bonded (similar to the method described above, but without coating).

In FIG. 4B, the thin-walled sleeve 58 is coated on the outer surface 54. For example, a desired liquid material 55 may be sprayed or brushed onto the outer surface 54, e.g., to provide a substantially uniform thickness hydrophilic or other coating on the outer surface 54. Alternatively, the coating may be applied by dipping the thin-walled sleeve 48 in a desired solution, e.g., a hydrophilic composition. In other alternatives plasma deposition, electrostatic deposition, vapor deposition, and the like may be used. If desired, the thin-walled sleeve may be positioned over a mandrel (not shown), pressurized, or otherwise supported to facilitate application of a desired liquid, solution, and/or coating.

Referring to FIG. 4C, the coated thin-walled sleeve 58 is then inverted so that the coated outer surface 54 and the inner surface 53 are now arranged on the interior and exterior of thin film sleeve 58, respectively. For example, the first end 57 of the thin-walled sleeve 58 may be pulled inwardly through the thin-walled sleeve 58 and out the second end 59. Thus, the coated surface now occupies the interior of the thin-walled sleeve 58.

Turning to FIG. 4D, a tubular structure 52 may then be attached to or around the inverted thin-walled sleeve 58 to provide a tubular device 56. Similar to the previous embodiments, the inverted thin-walled sleeve 58 may be positioned over a mandrel 50. The tubular structure 52 may then be positioned over the inverted thin-walled sleeve 58, thereby capturing the thin-walled sleeve 58 within the lumen 52a.

In the embodiment shown in FIG. 4D, the tubular structure 52 may be a slotted tube defining a lumen 52*a*, and including longitudinal edges 51*a*, 51*b* defining a slot therebetween that communicates with the lumen 52*a*. The tubular structure 52 may be formed from one or more layers, as described elsewhere herein. The tubular structure 52 may be formed as a generally "C" shaped cross-section, e.g., by extrusion, injection molding, lay-up, and the like. Alternatively, the tubular structure 52 may be formed as a continuous-walled tube, which may be slit or otherwise cut to create the slot and the longitudinal edges 51*a*, 51*b*.

To position the tubular structure 52 around the inverted thin-walled sleeve 58, the longitudinal edges 51*a*, 51*b* may be separated away from one another sufficient distance to allow the mandrel 50 and thin-walled sleeve 58 thereon to pass between the longitudinal edges 51*a*, 51*b* and enter the lumen 52*a*. In one embodiment, the diameter of the lumen 52*a* may be slightly smaller than the outer diameter of the thin-walled sleeve 58 on the mandrel 50. This embodiment may ensure that the tubular structure 52 is fitted snugly around the thin-walled sleeve 58.

The tubular structure 52 and the inverted thin-walled sleeve 58 may then be bonded or otherwise attached to one another. For example, similar to the previous embodiment, heat shrink tubing (not shown) may be positioned around the tubular structure 52 and heated to cause the shrink tubing to heat and/or compress radially inwardly the tubular structure 52. Alternatively, the entire assembly may be directed through a heated die.

This may cause the tubular structure 52 to at least partially melt or reflow, thereby fusing or otherwise bonding the longitudinal edges 51*a*, 51*b* together to provide a continuous wall. In addition, the heating may reflow, fuse, or otherwise bond the inverted thin-walled sleeve 58 to the inner surface of the tubular structure 52. Optionally, other processes may be used, such as delivering ultrasonic energy, lamination, and/or applying adhesives to attach the tubular structure 52 around the inverted thin-walled sleeve 58.

As shown in FIG. 4D, the resulting tubular device 56 (having lubricious inner surface 56*a*) is removed from the mandrel 50. Optionally, other components (not shown) may be added to the tubular device 56, as described elsewhere herein.

Figure 4E:
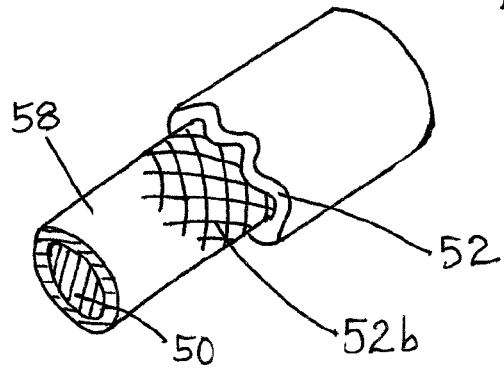

Turning to FIG. 4E, another method is shown for attaching a tubular structure 52 over the inverted thin-walled sleeve 58. After positioning the inverted thin-walled sleeve 58 around a mandrel 50, a reinforcement layer 52*b* may be applied around the inverted thin-walled sleeve 58. For example, one or more wires, filaments, or other strands may be wound or otherwise positioned around the inverted thin-walled sleeve 58, e.g., in a braided pattern (shown in FIG. 4E) or in a helical pattern (not shown).

A tubular structure 52 may then be applied around the reinforcement layer 52*b*. The tubular structure 52 may include one or more layers applied successively around the reinforcing layer 52*b*. For example, filament wound fibers and polymeric material (not shown) may be wound around the reinforcing layer 52*b* or thermoplastic or other flowable material may be extruded or otherwise directed around the reinforcing layer 52*b*.

Figure 4F:
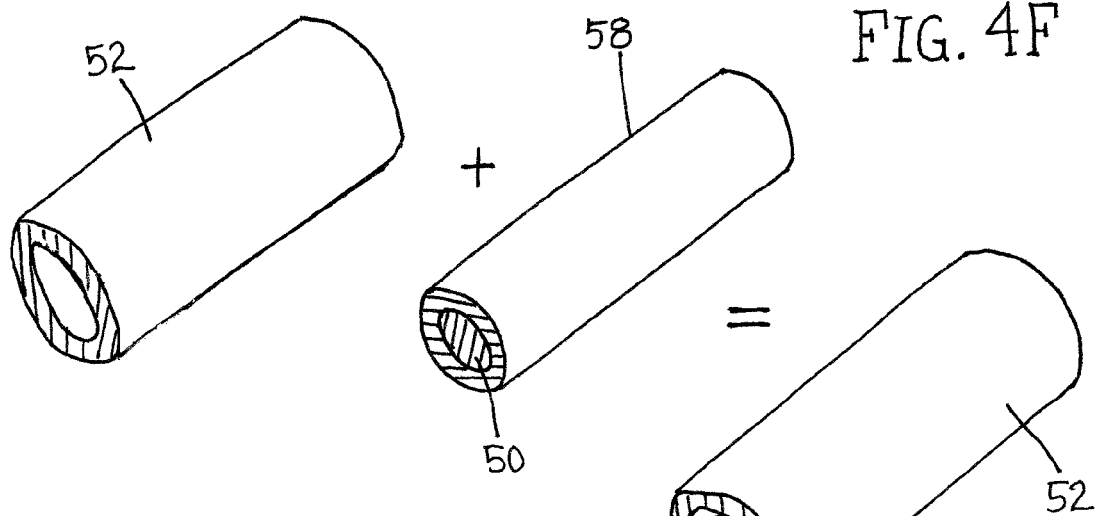
Figure 4G:
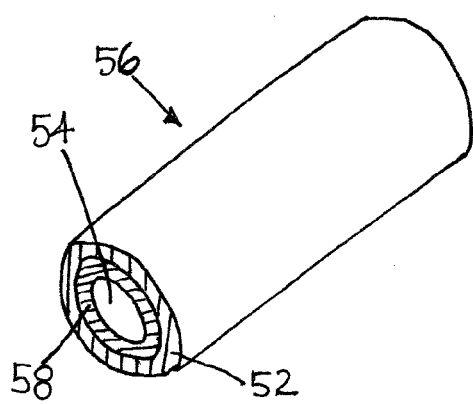

Turning to FIG. 4F, an alternative method is shown for attaching the tubular structure 52 around the inverted thin-walled sleeve 58. In this embodiment, the tubular structure 52 is a completely formed tube that may be positioned over and bonded to the inverted thin-walled sleeve 58. For example, an adhesive may be applied around the inverted thin-walled sleeve 58, and the tubular structure 52 may be advanced over the adhesive. The adhesive may then be cured, e.g., by heating, pressure, ultraviolet light exposure, and/or allowing sufficient time to cure. The mandrel 50 may then be removed, e.g., to provide the tubular device 56 shown in FIG. 4G.

Turning to FIG. 5A-5F, still another method is shown for making a tubular device, such as apparatus 10 described above. As shown FIG. 5A, a thin-walled sheet 68 may be provided that includes a first upper surface 64, a second lower surface (not shown), and opposing longitudinal edges 69*a*, 69*b*. The thin-walled sheet 68 may comprise materials and configurations, similar to other embodiments described elsewhere herein.

The first surface 64 of the thin-walled sheet 68 is coated, as described elsewhere herein, to provide a desired coating having one or more desired properties on the first surface 64. In an exemplary embodiment, the one or more desired properties includes a predetermined lubricity on the first surface 64, e.g., provided by a hydrophilic coating, such as those described elsewhere herein.

Figure 5A:
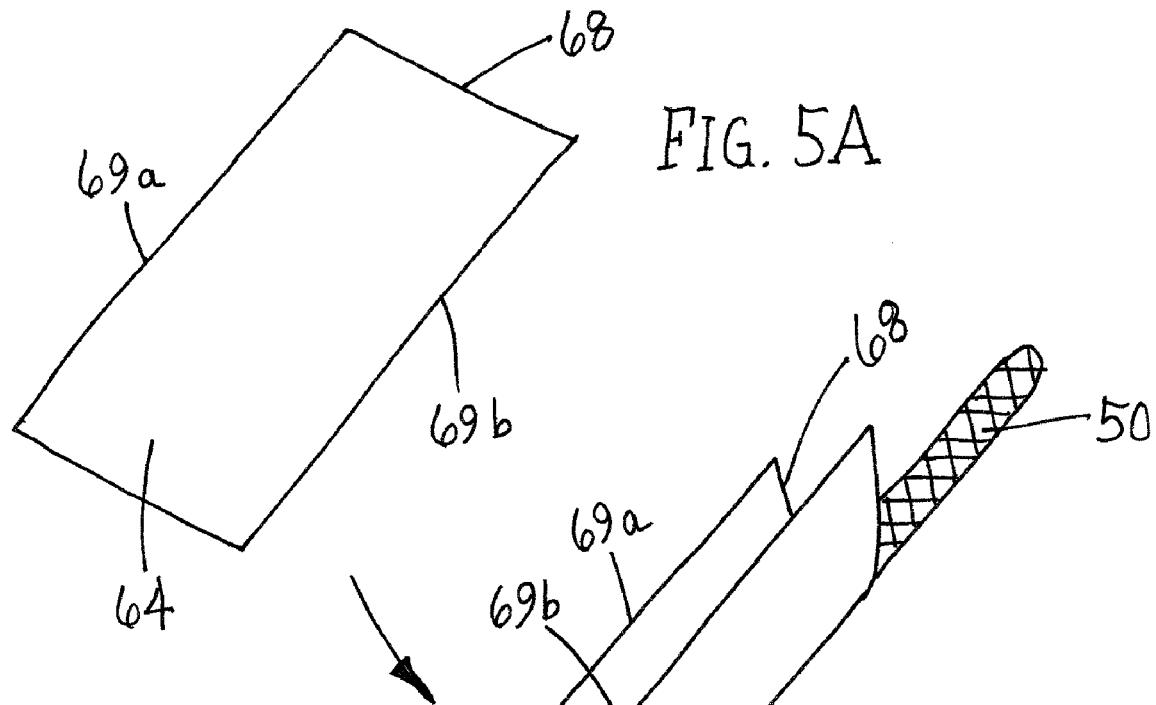
FIGS. 5A-5C are perspective views and FIGS. 5D-5F are cross-sectional views, showing another method for making a tubular device including a coated inner surface.
Figure 5B:
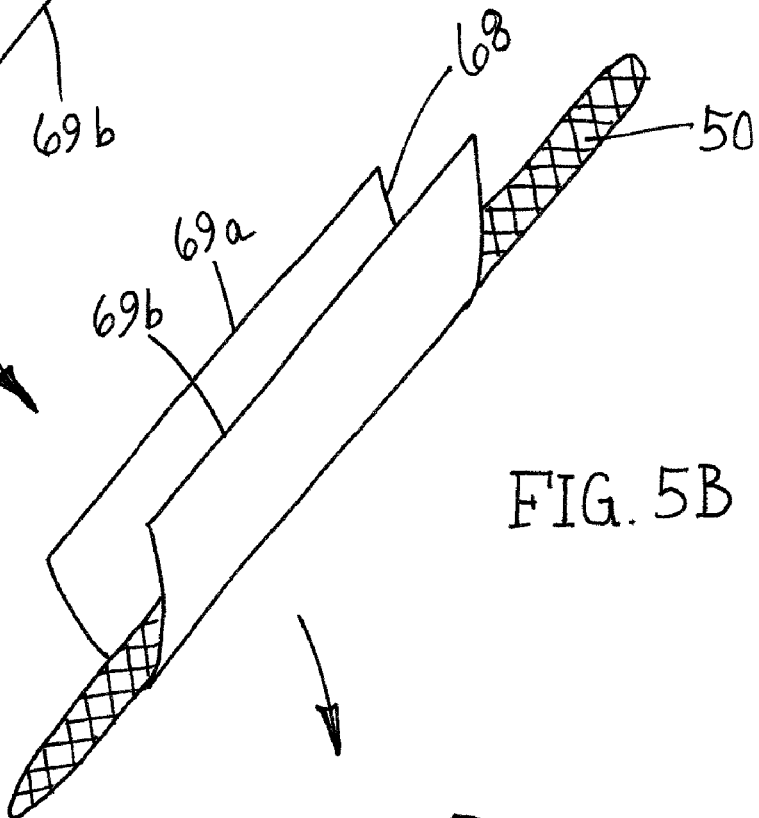
Figure 5C:
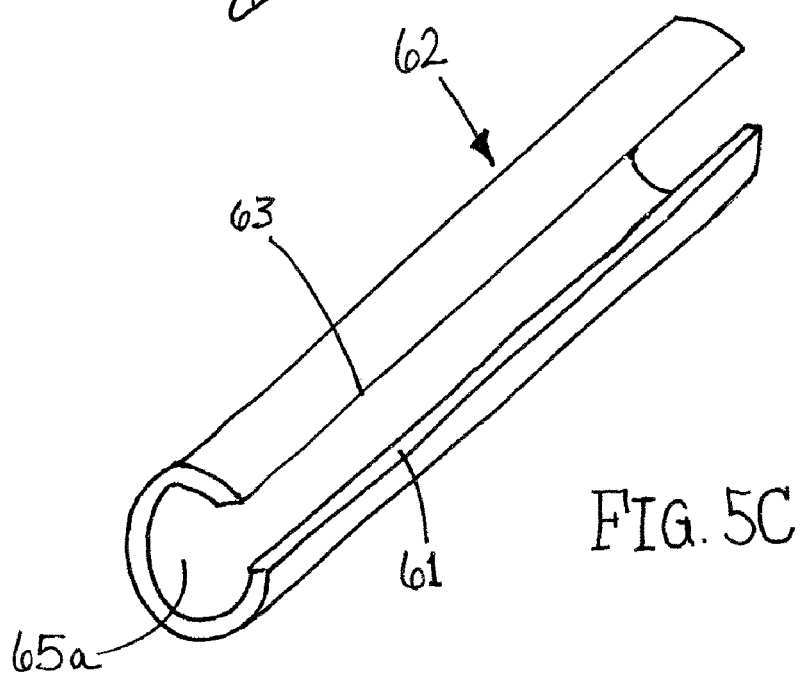

Turning to FIG. 5B, the thin-walled sheet 68 is partially wrapped around a mandrel 50 (which may be similar to other embodiments described herein) such that the first surface 64 is disposed inwardly towards the mandrel 50. As shown in FIG. 5C, a slotted tube 62 may be provided that may be formed similar to the embodiments described elsewhere herein. Thus, the slotted tube 62 may include opposing longitudinal edges 61, 63 defining a slot communicating with a lumen 65 of the slotted tube 62.

Figure 5D:
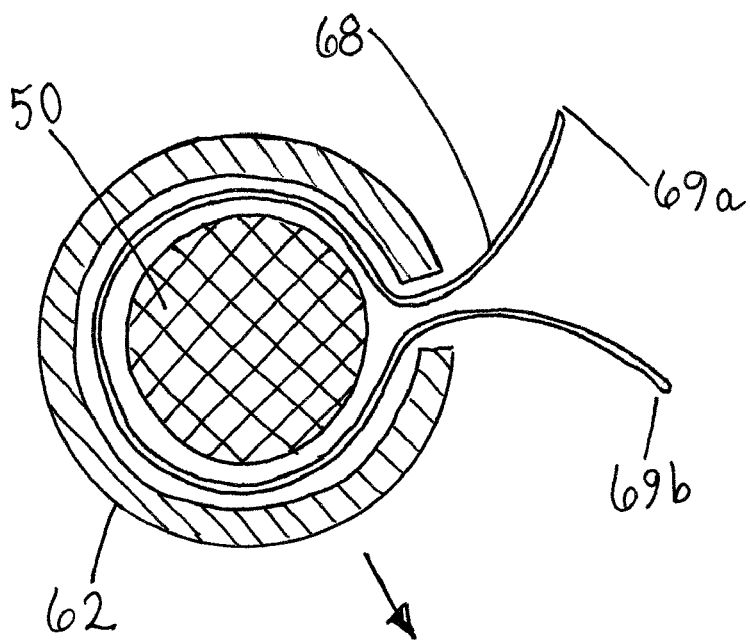

Turning to FIG. 5D, the slotted tube 62 may be positioned around the thin-walled sheet 68 by separating the longitudinal edges 61, 63 sufficiently to insert the mandrel 50 and thin-walled sheet 68 through the slot and into the lumen 65. As shown, the longitudinal edges 69*a*, 69*b* of the thin-walled sheet 68 may extend out from between the longitudinal edges 61, 63 of the slotted tube 62.

The slotted tube 62 may then be attached to the thin-walled sheet 68, e.g., by heat-sealing, advancement through a heated die or other lamination, bonding, and the like, as described elsewhere herein. For example, heating of the assembly may cause the material of the slotted tube 62 to at least partially reflow, thereby fusing or otherwise bonding the longitudinal edges 61, 63 together. For example, similar to previous embodiments, the assembly may be heated to attach the thin-walled sheet 68 to the inner surface of the slotted tube 62 and within the slot.

Figure 5E:
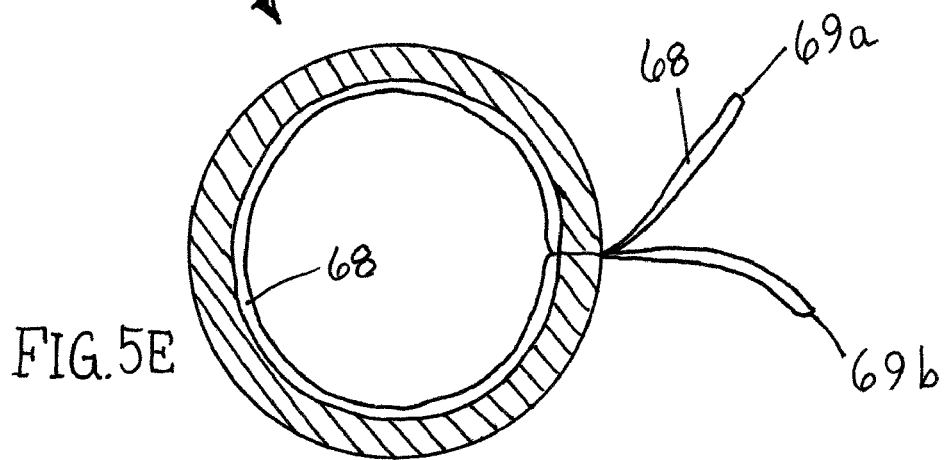
Figure 5F:
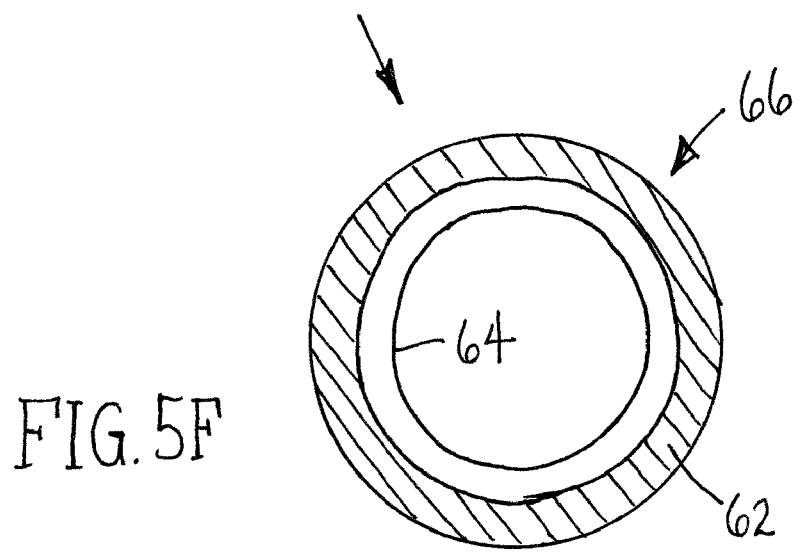

Excess material from the longitudinal edges 69*a*, 69*b* of the thin-walled sheet 68 may remain exposed outside the (no longer slotted) tube 62. This excess material may be cut or otherwise trimmed along the wall of the tube 62, resulting in the tubular device 66 shown in FIG. 5F. As shown in FIG. 5E, the mandrel 50 is removed from the bonded thin film sheet 68 and slotted tube 62, either before or after trimming the excess longitudinal edges 69*a*, 69*b*.

Turning to FIG. 6A-6E, yet another method is shown for making a tubular device, such as apparatus 10 described above. As shown in FIG. 6A, a relatively thick sheet 78 may be provided that includes a first upper surface 74, a second lower surface 75, first and second side edges 77*a*, 77*b*, and a thickness 79. The sheet 78 may be formed from one or more layers of material, similar to the tubular structures described elsewhere herein, except provided in a relatively flat configuration (or a concave, convex, or other nonplanar configuration where the first surface 74 is readily accessible, similar to other embodiments herein). In exemplary embodiments the thickness 79 of the sheet 78 may be between about 0.0005-0.2 inch (0.0127-5.08 mm).

Turning to FIG. 6B, the first surface 74 of sheet 78 is coated, e.g., similar to the methods describe elsewhere herein, to provide a substantially uniform thickness coating 88 on the first surface 74. For example, the coating 88 may include a hydrophilic material that provides a desired lubricity to the first surface 74.

As shown is FIGS. 6C and 6D, the coated sheet 78 may be positioned near and rolled around a mandrel 50, which may be similar to other embodiments described herein, with the coated first surface 74 disposed inwardly. As seen in FIG. 6D, after rolling the coated sheet 78, the first side edge 77a may be disposed adjacent the second side edge 77b, thereby providing a tubular structure defining a lumen. The first and second side edges 77a, 77b may then be bonded or otherwise attached to one another, e.g., using heat bonding, lamination, ultrasonic energy, or adhesives, as described elsewhere herein.

As shown in FIG. 6E, once the side edges 77a, 77b are attached to provide a continuous wall tubular device 76, the tubular device 76 may be removed from the mandrel 50, thereby resulting in the tubular device 76 having the lubricious inner surface 74.

Figure 7:
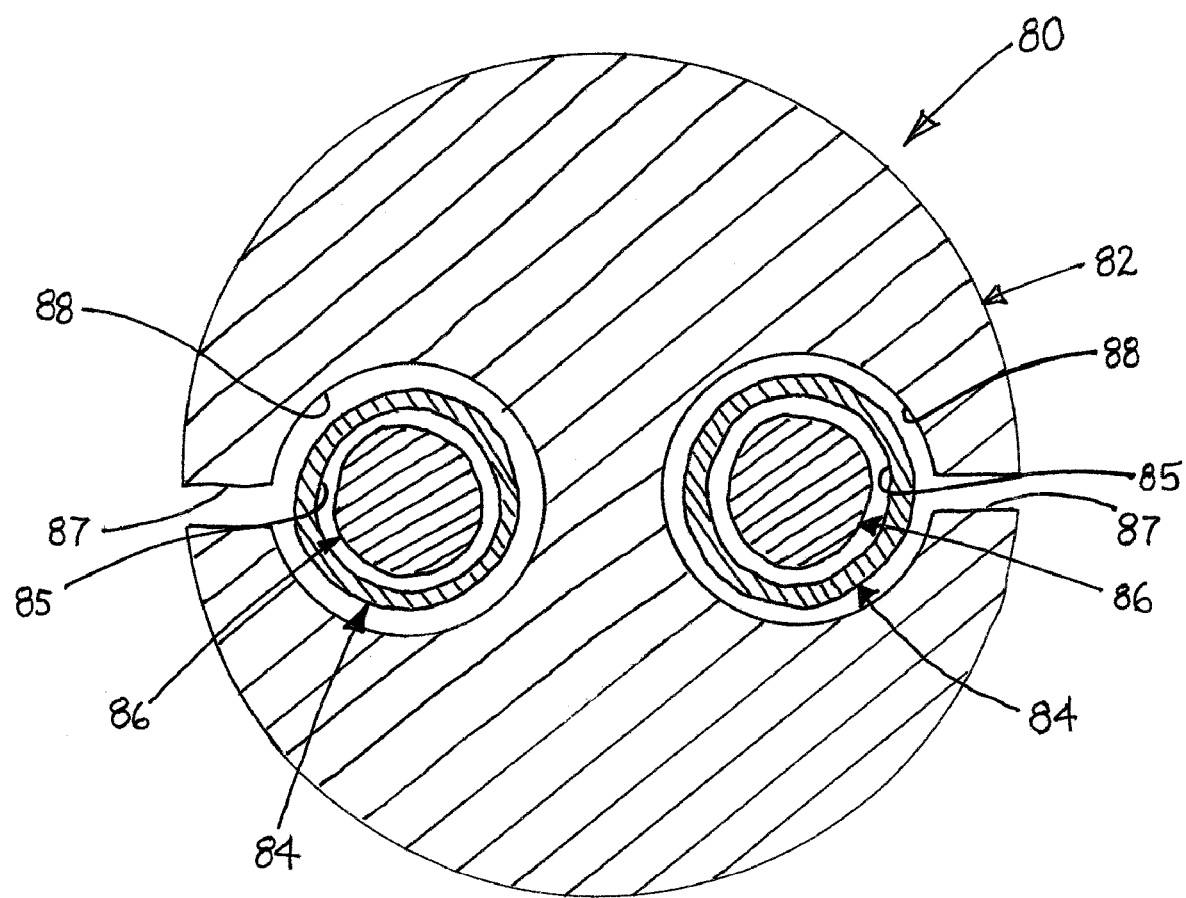
FIG. 7 is a cross-sectional view of a tubular device including a pair of adjacent lumens disposed over a mandrel carrying a coated thin-walled sleeve.

Turning to FIG. 7, another embodiment of a tubular assembly 80 is shown that includes an outer tubular body 82, a pair of thin-walled sleeves 84, and a pair of mandrels 86. Similar to the embodiments described elsewhere herein, the thin-walled sleeves 84 may be formed from flat sheets or tubular sleeves that have a coating on an inner surface 85 thereof. For example, the coating may be applied before the sheet is rolled and formed into the sleeves 84 or while the sleeves 84 are in a tubular form (e.g., by coating an outer surface and inverting the sleeves 84). The sleeves 84 may be positioned around respective mandrels 86, which may also be similar to other embodiments herein.

As shown, the outer tubular body 82 includes a pair of lumens 88 extending longitudinally through the tubular body 82. The tubular body 82 may be an extrusion or other single or multiple layer tubular structure, similar to other embodiments described herein. For example, the tubular body 82 may be formed as a continuous walled tube, which may be slit along its length to provide slots 87 communicating with respective lumens 88.

The tubular body 82 may be positioned around the mandrels 86 and thin-walled sleeves 84, similar to the previous embodiments. For example, each slot 87 may be opened sufficiently to insert a mandrel 86 carrying a thin-walled sleeve 84 through the slot 87 into the lumen 88. Alternatively, the mandrels 86 may be inserted longitudinally into the respective lumens 88 with the thin-walled sleeves 84 thereon. In this alternative, it may be possible to eliminate the slots 87 or the slots 87 may facilitate advancement by allowing the lumens 88 to be temporarily expanded. The tubular body 82 may be attached to the thin-walled sleeves 84, e.g., by heating as described above, thereby reflowing the material of the tubular body 82 to close the slots 87 and provide a continuous wall structure. The mandrels 86 may then be removed, thereby providing a tubular device having lumens 88 having coated inner surfaces. Thus, it will be appreciated that tubular devices may be created that include multiple lumens, each of which may include a desired coating along its inner surface.

Figure 8:
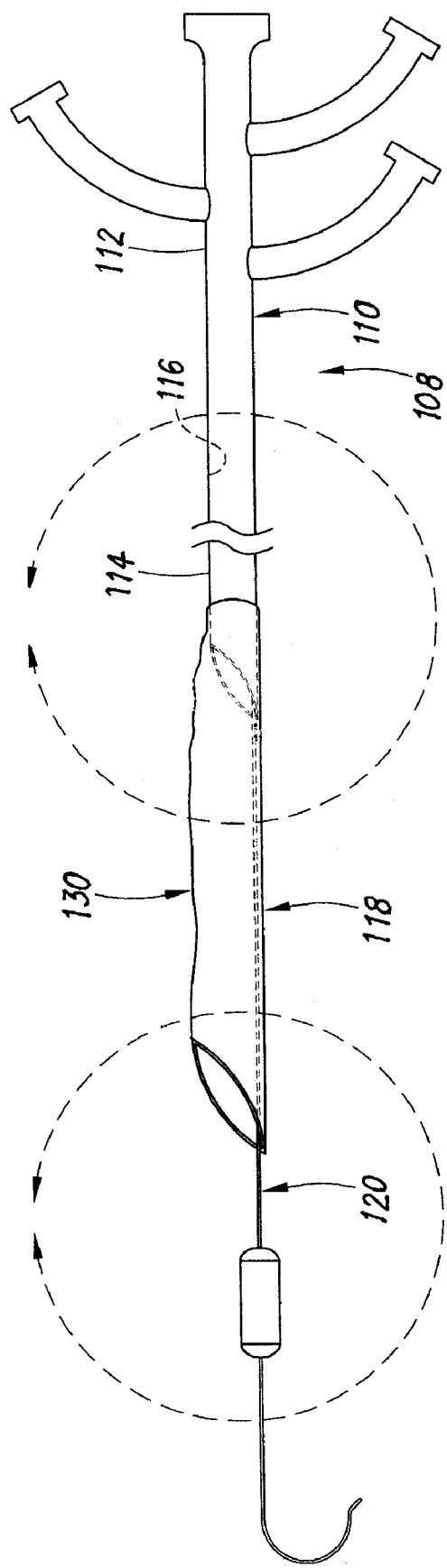
FIG. 8 is a perspective view of an exemplary embodiment of a sheath apparatus, including a tubular proximal portion and an expandable distal portion. The tubular portion includes a lumen with a coated inner surface.

Turning to FIG. 8, an exemplary embodiment of a sheath apparatus 108 is shown that includes a tubular proximal portion 110 and an expandable distal portion 118. The proximal portion 110 may include at least one lumen 116 including a coated liner (not shown), such as any of the embodiments described herein.

Generally, the proximal portion 110 is an elongate tubular member, e.g., a catheter, sheath, and the like, including a proximal end 112, a distal end 114 sized for insertion into a body lumen, and a lumen 116 extending between the proximal and distal ends 112, 114. Optionally, the tubular proximal portion 110 may include one or more additional lumens (not shown), e.g., for receiving a guide wire, inflation media, and/or for perfusion. Such additional lumens may be disposed concentrically around one another or in a side-by-side arrangement.

With continued reference to FIG. 8, the expandable distal portion 118 may include an elongate stiffening member 120 providing a "backbone" for the distal portion 118 and an expandable sheath 130. Additional information on materials and methods for making the apparatus 108 are disclosed in co-pending application Ser. Nos. 10/423,321, filed Apr. 24, 2003, Ser. No. 10/934,082, filed Sep. 2, 2004, Ser. No. 10/934,305, filed Sep. 2, 2004, and Ser. No. 10/958,034, filed Oct. 4, 2004. The entire disclosures of these references are expressly incorporated by reference herein.

Figure 9:
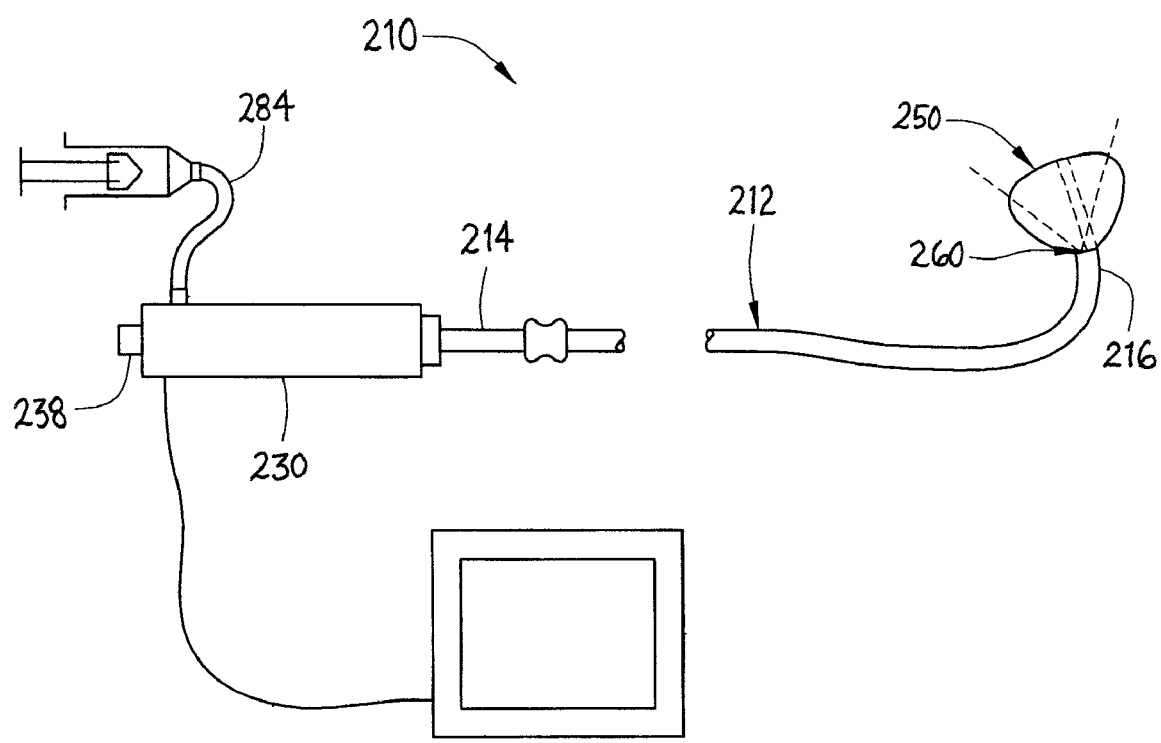
FIG. 9 is a perspective view of an imaging catheter including a lumen, the lumen including a coated inner surface.

Turning to FIG. 9, an exemplary embodiment of an apparatus 210 is shown for imaging a body lumen, e.g., for visualizing, accessing, and/or cannulating a body lumen from a body cavity (not shown). Generally, the apparatus 210 includes a catheter or other elongate member 212, including a handle 230 on a proximal end 214 of the catheter 212, and a balloon or other expandable member 250 on a distal end 216 of the catheter 212. An imaging assembly 260 may be provided on or otherwise carried by the catheter 212 for imaging through the balloon 250, e.g., including one or more illumination fibers and/or imaging optical fibers (not shown) extending through the catheter 212.

The catheter 212 may include one or more lumens (not shown) extending between the proximal and distal ends 214, 216 that may include a coated liner or inner surface, as described elsewhere herein. For example, an accessory lumen (not shown) may extend from a port 238 in the handle 230 through the balloon 250. The lumen may be coated or otherwise lined to facilitate introducing one or more instruments (not shown) the through the apparatus 210.

Additional information that may relate to the structure and/or methods for making and/or using the apparatus 210 may also be found in co-pending application Ser. Nos. 10/447,526, filed May 29, 2003, Ser. No. 11/057,074, filed Feb. 11, 2005, and Ser. No. 11/062,074, filed Feb. 17, 2005. The entire disclosures of these references are expressly incorporated by reference herein.

Returning to FIGS. 1A and 1B, in another embodiment, a delivery sheath 10 may be provided that includes an inner polyurethane liner 20 having a coating on its inner surface 21. In an exemplary embodiment, the liner 20 may have a thickness between about 0.0001-0.01 inch (0.0127-0.25 mm), or between about 0.0001-0.003 inch. The coating may include any of the embodiments described herein, e.g., a lubricious and/or hydrophilic material applied using any of the methods described herein. For example, the inner liner 20 may be formed from a coated sheet or an inverted tube, as described elsewhere herein.

The sheath 10 may include an outer layer 22 that includes a stainless steel braid (not shown) surrounding the inner liner 20 and a layer of PEBAX or urethane surrounding the braid. In an exemplary embodiment, the layer of PEBAX or urethane may have a thickness between about 0.004-0.02 inch (0.1-0.5 mm). The sheath 10 may define a lumen 16 having a diameter between about one and five millimeters (1-5 mm), depending upon the particular application for the sheath 10.

With continued reference to FIGS. 1A and 1B, in another embodiment, the device 10 may be a core for passage of a guidewire (not shown). In such an embodiment, the inner liner 20 may include a layer of polyurethane having a thickness between about 0.0001-0.0015 inch (0.0025-0.038 mm) thickness. An inner surface 21 of the liner 20 may be coated as described elsewhere herein, e.g., with a lubricious and/or hydrophilic materials. The outer layer 22 may include a tubular body formed from nylon, PEBAX, or urethane having a thickness between about 0.0005-0.006 inch (0.0127-0.076 mm). The resulting device 10 may include a lumen 16 having a diameter between about 0.016-0.045 inch (0.40-1.15 mm).

The device 10 may be provided within a catheter, guidewire, or other tubular device (not shown), which may be constructed in any known manner. The device 10 may be bonded or otherwise attached within a lumen of the tubular device, similar to the methods described above, to provide a lubricious or otherwise coated inner lumen 16.

Figure 10A:
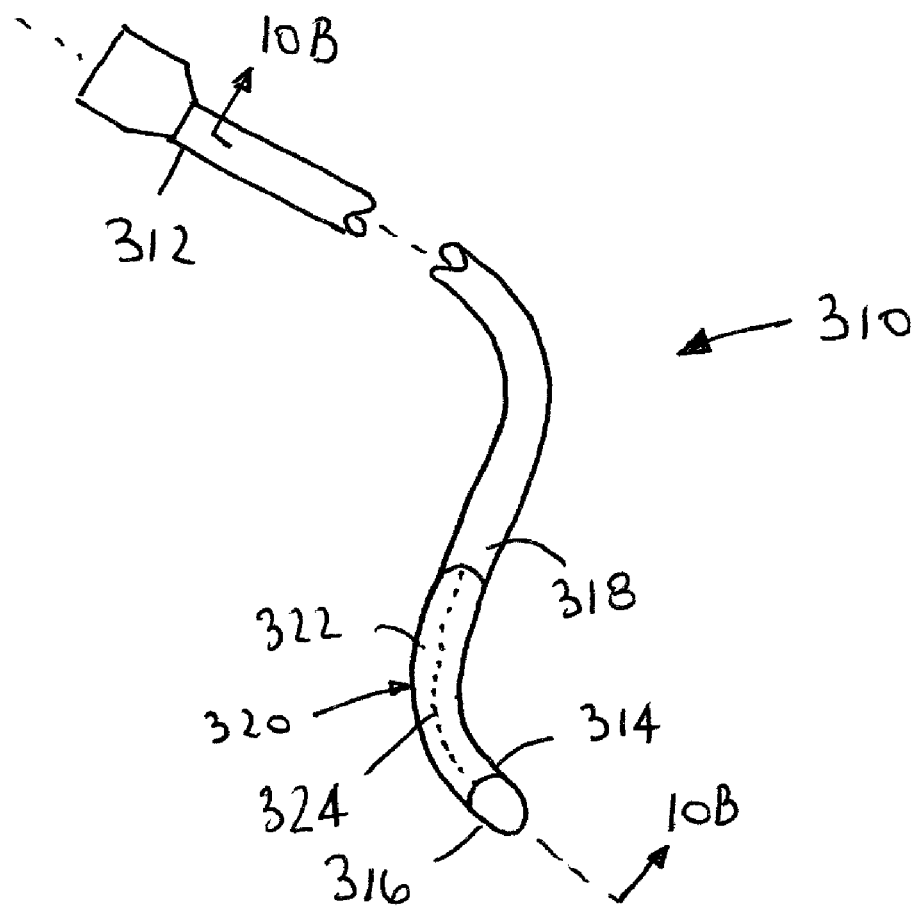
FIG. 10A is a perspective view of an elongate lead including an outer lubricious coating on a portion thereof.
Figure 10B:
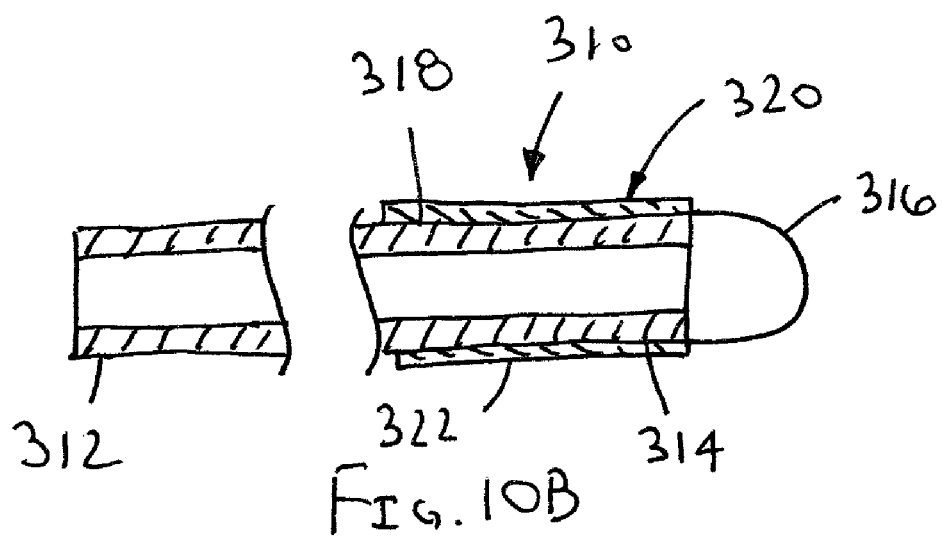
FIG. 10B is a cross-sectional view of the lead of FIG. 10A taken along line 10B-10B.

Turning to FIGS. 10A and 10B, in yet another embodiment, an elongate lead 310 is shown that includes a proximal end 312, a distal end 314 sized and/or shaped for introduction into a patient's vasculature, and one or more electrodes 316 (one shown) on the distal end 314. The lead 310 is formed from a lead body, which may be formed, for example, from silicone, polyurethane, or other materials defining an outer surface 318. The lead body may have a uniform construction along its length or may vary, similar to other embodiments described herein. The lead 310 may include other components, e.g., one or more wires or other conductors (not shown) extending between the electrode(s) and the proximal end 312, one or more mechanical and/electrical connectors (also not shown) on the proximal end 312, and the like.

The lead 310 includes an outer cover 320 surrounding at least a portion of the outer surface 318. The cover 320 may include a layer of polyurethane, e.g., having a thickness between about 0.00025-0.003 inch (0.0127-0.076 mm). The cover 320 includes a coating on its outer surface 322, which may be any of the coatings described herein, e.g., including a lubricious and/or hydrophilic material.

As best seen in FIG. 10A, the cover 320 extends along the distal end 314 of the lead 310, e.g., immediately adjacent the electrode 316. Alternatively, the cover 320 may extend over the electrode 316 (not shown). In addition or alternatively, the cover 320 may extend proximally from the distal end 314 towards the proximal end 312 (also not shown). In other alternatives, a plurality of covers (not shown) may be provided spaced apart from one another along the length of the lead 310. The covers may include similar or different coatings from one another, depending upon the properties desired for different portions of the lead 310.

As shown in FIG. 10A, the cover 320 may include a weakened seam 324 extending along a length of the cover 320. The seam 324 may be a thin-walled region, a perforated seam, and the like. Optionally, a plurality of weakened seams (not shown) may be provided. The seam 324 may facilitate removal of the cover 320, if desired. In addition, a thread, tab, or other element (not shown) may extend from the cover 320, e.g., to the proximal end 312 of the lead 310. Such an element may be grasped or otherwise manipulated to remove the cover 320, e.g., pulled to cause the seam 324 to tear and peel the cover 320 from around the lead 310.

The cover 320 may be made similar to the liners described above, e.g., as a sheet or tube (but without being inverted). The cover 320 may be simply slid over the lead 310, heat shrunk around the lead 310, or bonded onto the outer surface 318 (depending upon whether the cover 320 is removable).

During use, the lead 310 may be introduced using conventional methods. The cover 320 may facilitate advancing the distal end 314 through tortuous anatomy, e.g., if the cover 320 includes a lubricious coating. Once the lead 310 is positioned at a desired location, the cover 320 may be removed from over the distal end 314. For example, as described above, a tab (not shown) adjacent the proximal end 312 and coupled to the cover 320 may be pulled to tear or otherwise remove the cover 320. Removing the cover 320 may facilitate maintaining the distal end 314 at the desired location, i.e., minimizing migration that may occur of the cover remains over the distal end 314. Optionally, the underlying outer surface 318 of the lead 310 may include materials, features, coatings, and the like that enhance securing the distal end 314 once the cover 320 is removed.

Figure 11A:
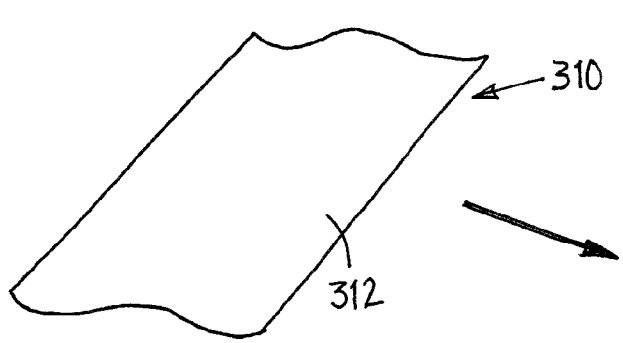
FIGS. 11A-11F are perspective views and FIG. 11G is a cross-sectional view, showing another method for making a tubular device including a coated inner surface.

Turning to FIGS. 11A-11G, another method is shown for making a tubular device, such as apparatus 10 described above. Initially, as shown in FIG. 11A, a thin film sheet 310 may be provided including a first upper surface 312 and a second lower surface 314 (not shown in FIG. 11A, see, e.g., FIG. 11C). The sheet 310 may be formed from a single layer or multiple layers of material, similar to the other embodiments described elsewhere herein. In an exemplary embodiment, the sheet 310 may be formed from a sheet of polyurethane, e.g., having a thickness between about 0.0001-0.003 inch (0.0025-0.076 mm). However, other suitable polymers may also be used.

Figure 11B:
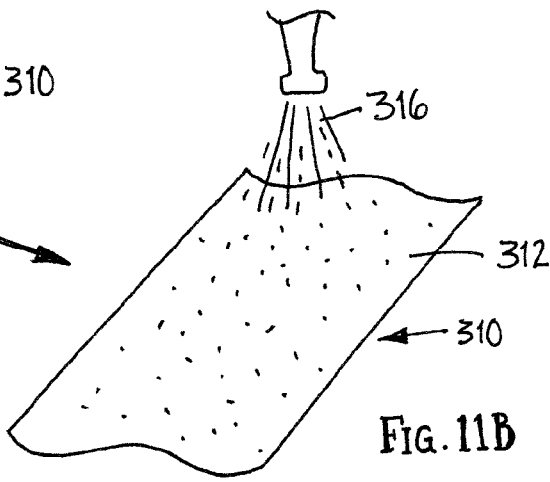

Turning to FIG. 11B, with the sheet 310 substantially flat (or otherwise providing ready access to first surface 312, as described elsewhere herein), a coating 316 is applied to the first surface 312. Alternatively, a pre-formed thin membrane sleeve may be coated on its outer surface and subsequently inverted, as described elsewhere herein. In an exemplary embodiment, the coating may include a hydrophilic material, such as Polyvinylpyrrolidone, sprayed onto the first surface 312. Alternatively, the coating may be applied using other procedures, such as rolling, brushing, spreading by maer rods, or dipping, e.g. on the first surface 312.

The hydrophilic material may provide a predetermined lubricity on the first surface 312. Alternatively or in addition, other materials may be applied to provide one or more desired properties on the first surface 312, e.g., anti-thrombotic or anti-hemolytic materials, drug-eluting coatings, and the like. Alternatively, these materials may also be applied to the second surface (not shown). As a further alternative, other materials, for example, adhesives, primers, reinforcing elements, backing material, and the like, may be applied to the second surface 314, e.g., to facilitate construction or processing of a thin-walled sleeve or a subsequent apparatus, as described elsewhere herein.

Figure 11C:
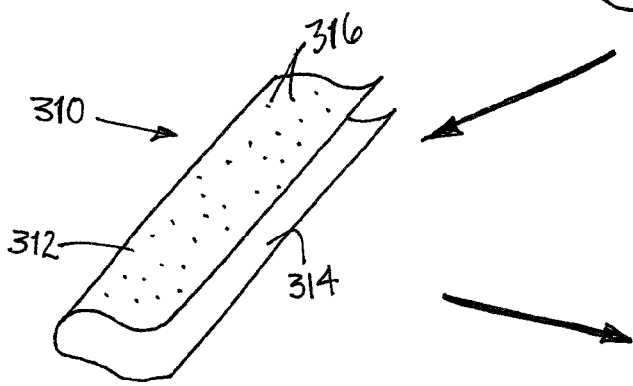
Figure 11D:
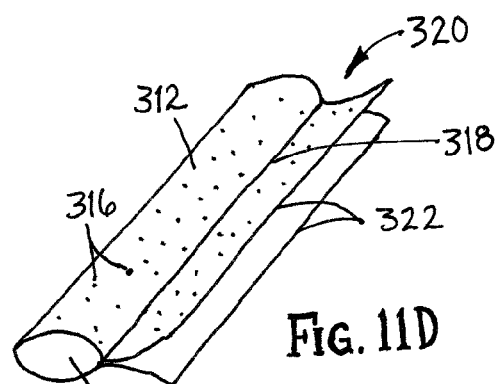
Figure 11E:
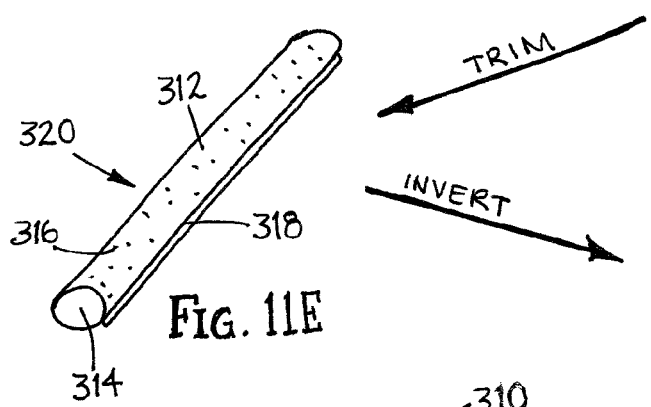

Turning to FIG. 11C, the sheet 310 may be folded over such that the first surface 312 is disposed outwardly and the second surface 314 is disposed inwardly. A longitudinal seam 318 may then be created to create a relatively thin-walled sleeve 320. For example, the longitudinal seam may be created by heat bonding, using ultrasonic energy, using one or more adhesives, and/or as otherwise described elsewhere herein. As shown in FIGS. 11C and 11D, excess material 322 may be trimmed from the thin-walled sleeve 320. Turning to FIG. 11E, the thin-walled sleeve 320 may then be inverted, as described elsewhere herein, such that the first surface 312 is now disposed inwardly.

Figure 11F:
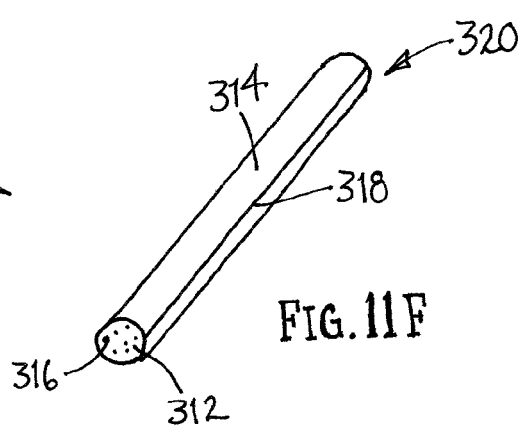
Figure 11G:
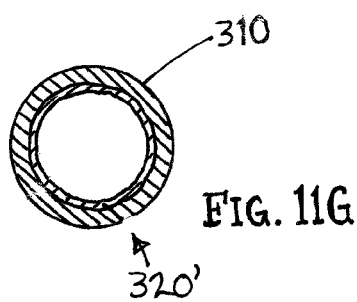

Turning to FIG. 11F, in an alternative embodiment, a thin-walled sleeve may be created by disposing the coated first surface 312' of the thin film sheet 310 inwardly before creating a longitudinal seam (not shown). Using this method, there is no need to invert the thin-walled sleeve 320' in order to dispose the coated first surface 312' inwardly. Optionally, one or more outer layers (not shown) may be bonded or otherwise provided around the thin-walled sleeve 320 or 320,' similar to the other embodiments described elsewhere herein.

Figures 12A, 12B:
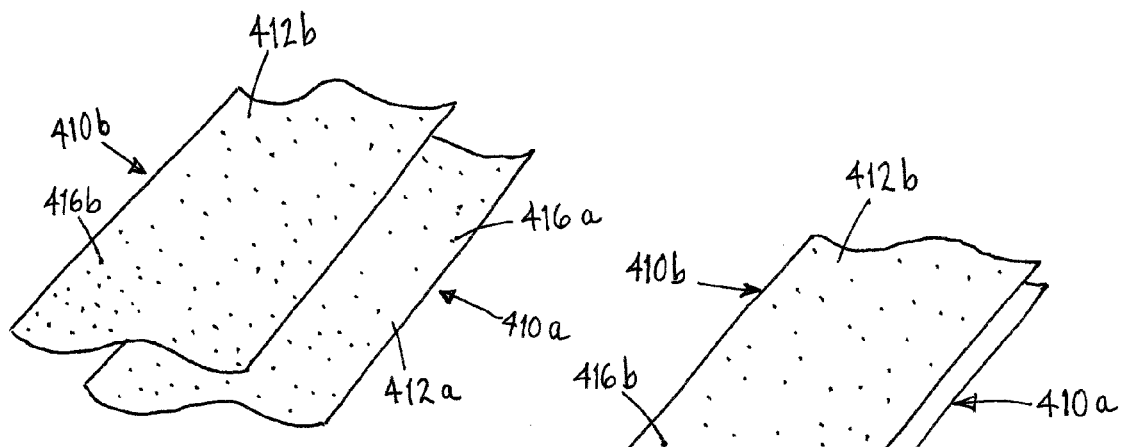
FIGS. 12A-12E are perspective views and FIG. 12F is a cross-sectional view, showing another method for making a tubular device including a coated inner surface.

Turning to FIGS. 12A-12F, another method is shown for making a coated thin-walled sleeve. Initially, as shown in FIG. 12A, two thin film sheets 410a, 410b may be provided, similar to other embodiments described herein. Each sheet 410a, 41b includes a first upper surface 412a, 412b and a second lower surface 414a, 414b (not shown in FIG. 12A). With each sheet 410 substantially flat, a coating 416 may be applied, as described elsewhere herein, to each first surface 412. Optionally, each second surface 414 may also be coated as described elsewhere herein.

Figures 12C, 12D:
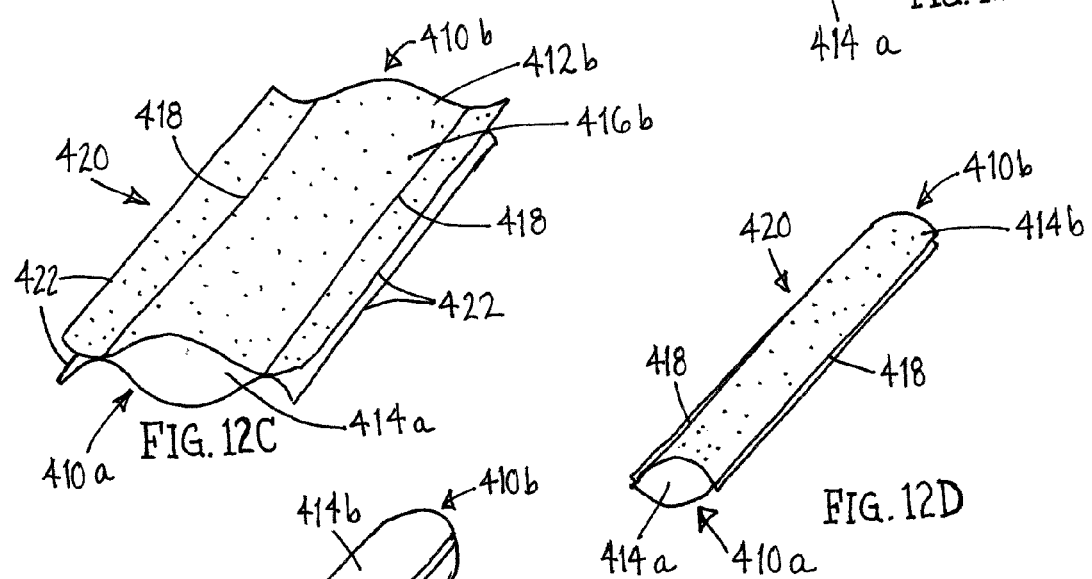
Figures 12E, 12F:
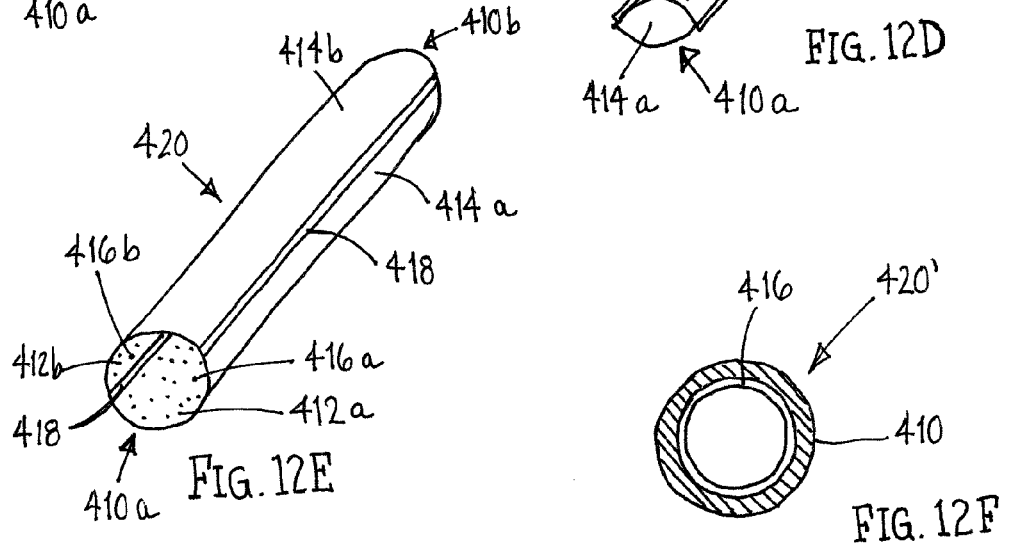

Turning to FIGS. 12B and 12C, the second surfaces 414 of sheets 410 may be placed adjacent to one another and at least two longitudinal seams 418 may then be created to form a relatively thin-walled sleeve 420. Excess material 422 may be trimmed from the thin-walled sleeve 420, as shown in FIG. 12D. Turning to FIG. 12E, the thin-walled sleeve 420 may then be inverted such that the first surfaces 412 are now disposed inwardly.

Turning to FIG. 12F, in an alternative embodiment, a thin-walled sleeve 320' may be created by disposing the coated first surfaces 412 of the thin film sheets 410 inwardly before creating the longitudinal seams (not shown). Using this method, there is no need to invert the thin-walled sleeve 420' in order to dispose the coated first surfaces 412 inwardly. In alternative embodiments, other methods may be used, such as those described elsewhere herein, which may include orienting a coated surface such that inversion is not required subsequent to seam creation in order to dispose the coated surface inwardly.

Figure 13A:
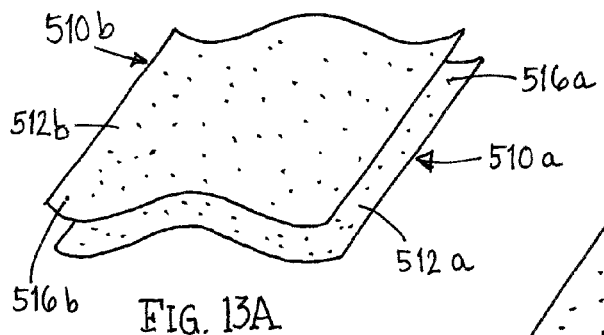
FIGS. 13A-E are perspective views and FIG. 13F is a cross-sectional view, showing another method for making a tubular device including a coated inner surface.

Turning to FIGS. 13A-13F, another method is shown for making coated thin-walled sleeves. Initially, as shown in FIG. 13A, two thin film sheets 510a, 510b may be provided similar to other embodiments wherein, each including a first upper surface 512a, 512b and a second lower surface 514a, 514b (not shown in FIG. 13A). With each sheet 510 substantially flat (or otherwise provided), a coating 516 is applied to each first surface 512, as described elsewhere herein. Optionally, each second surface 514 may also be coated, as described elsewhere herein.

Figure 13B:
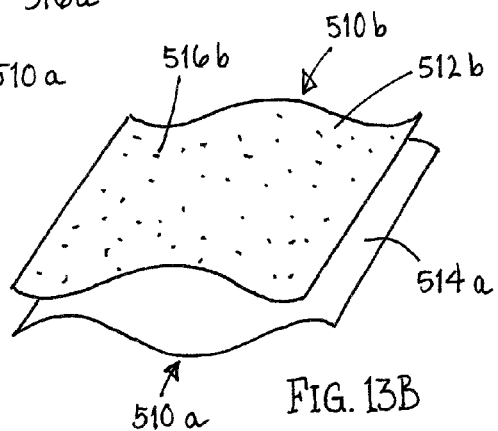
Figure 13C:
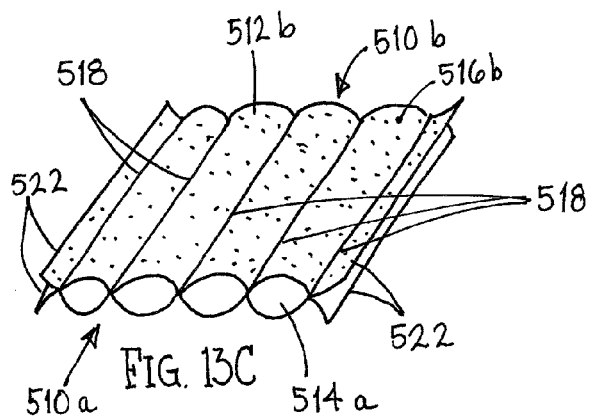
Figure 13D:
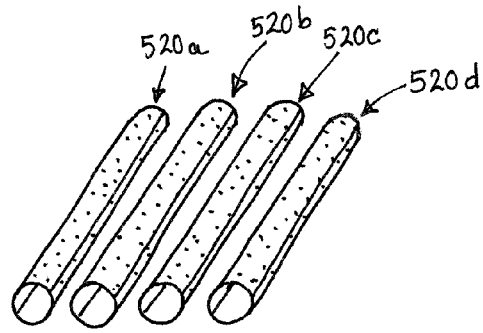
Figure 13E:
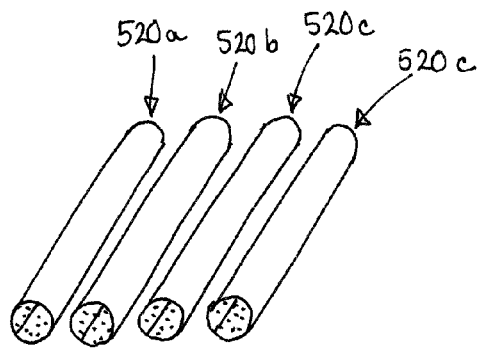

Turning to FIGS. 13B and 13C, the second surfaces 514 of sheets 510 may be placed adjacent to one another and a plurality of (e.g., at least three) longitudinal seams 518 may then be created to form at least two relatively thin-walled sleeves 520. The sleeves 520 may be separated and excess material 522 may be trimmed from the thin-walled sleeves 520, as shown in FIG. 13D. A longitudinal cut may be created at the same time each longitudinal seem 518 is created or subsequent to creating each longitudinal seam 518, thereby, separating adjacent thin-walled sleeves 520 from one another. Turning to FIG. 13E, each thin-walled sleeve 520 may be inverted such that the coated first surfaces 512 are now disposed inwardly.

Figure 13F:
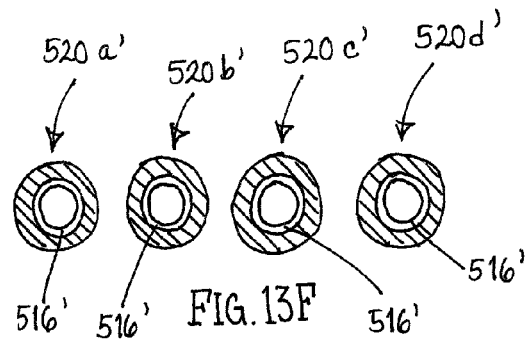

Turning to FIG. 13F, in an alternative embodiment, multiple thin-walled sleeves 520' may be created by disposing the coated first surfaces 516' of the thin film sheets inwardly creating longitudinal seams (not shown). Using this method, there is no need to invert the thin-walled sleeves 520' in order to dispose the coated first surfaces inwardly.

Figure 14A:
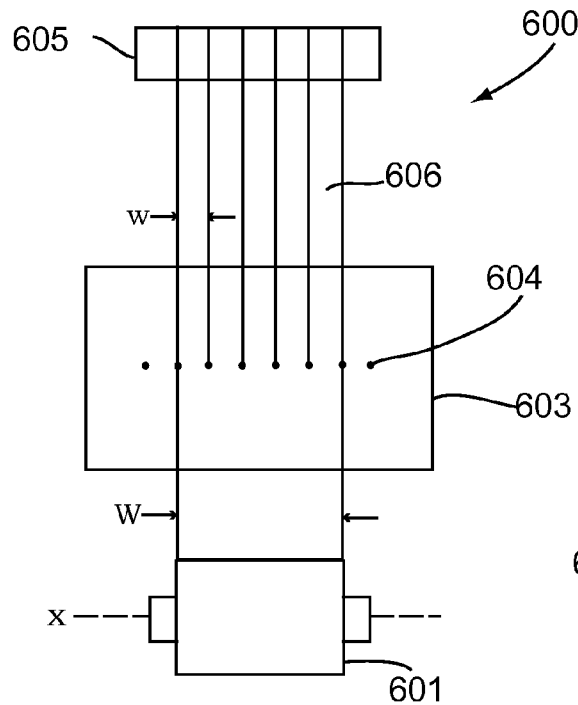
FIGS. 14A and 14B are top and side views, respectively, of an exemplary embodiment, showing an apparatus and method for making multiple thin-walled sleeves substantially simultaneously.
Figure 14B:
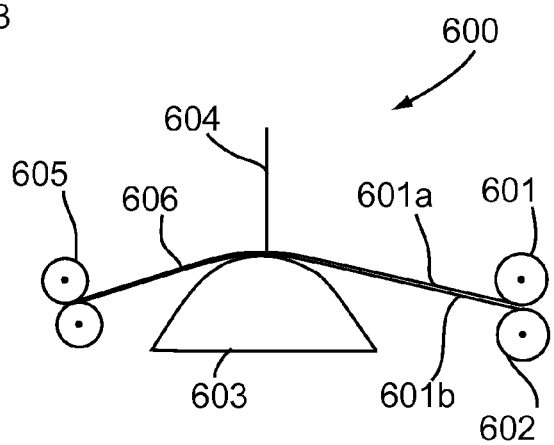

Turning to FIGS. 14A-14B, an exemplary embodiment of an apparatus 600 is shown for making multiple thin-walled sleeves 606 simultaneously, e.g., using a substantially continuous process. As shown, the apparatus 600 generally includes at least two source rollers 601, 602, a tensioning element 603, and one or more collecting rollers 605. The components of the apparatus 600 may be connected together by one or more frame or support structures (not shown) such that the components of the apparatus 600 are arranged substantially as shown. Alternatively, the components may be separate from one another but may be mounted and/or spaced apart from one another to provide the desired arrangement, such as that shown.

The source rollers 601, 602 may include axles, hubs, spools, and the like that are free to rotate about axis of rotation "x." The source rollers 601, 602 may carry source material wound thereon, e.g., one or more thin film sheets 601a, 602a, which may be fed through the apparatus 600 to make one or more thin-walled sleeves 606. For example, each sheet 601a, 602a may be similar to any of the sheets or materials described elsewhere herein, e.g., including one or more coatings on at least one surface. The source material may be wound or otherwise loaded directly onto the source rollers 601, 602, e.g., after forming and/or coating the source material, e.g., using methods similar to those described elsewhere herein, and/or after other previous processing. Alternatively, the source material may be provided on rolls (not shown), e.g., after coating or other processing of the source material. The rolls may be loaded onto axles or other structures (not shown) to provide the source rollers 601, 602.

The tensioning element 603 is spaced apart from the source rollers 601, 602 and includes one or more, e.g., at least two, cutting and/or sealing elements 604. For example, the tensioning element 603 may include a ridge along which the cutting/sealing elements 604 are aligned, e.g., such that the cutting/sealing elements 604 define an axis that is substantially parallel to the axis of rotation "x" of the source rollers 601, 602. The cutting/sealing elements 604 may include one or more elements for separating the sheets 601a, 602a passing over the tensioning element 603 into individual strips and/or may bond edges of the adjacent strips to form the thin-walled sleeves 606. In exemplary embodiments, the cutting/sealing elements 604 may include wires, ribbons, or blades, which may be heated, vibrated or otherwise operated to bond edges of the sheets 601a, 601b, as described further below.

The collecting roller(s) 605 may be aligned with and/or spaced apart from the tensioning element 603, e.g., opposite the source rollers 601, 602. The collecting roller(s) 605 may be driven by one or more motors or other drives (not shown), which may pull the sheets 601a, 602a from the source rollers 601, 602 through the tensioning element 603, and onto the collecting roller(s) 605.

In one embodiment, individual collecting rollers 605 may be provided for substantially continuously receiving respective individual thin-walled sleeves. In this embodiment, each collecting roller 605 may have a width corresponding to the width of the individual thin-walled sleeves. The collecting rollers 605 may be arranged parallel to one another, e.g., defining a common axis of rotation, which may ensure that the tension applied to the sleeves is substantially uniform. Alternatively, the collecting rollers 605 may be located in other configurations, although tension adjustment devices may be required to ensure that the tension applied to the sheets 601a, 602a and sleeves are substantially uniform.

In a further alternative, a single collecting roller 605, driven by a single motor or drive, may be provided for receiving all of the thin-walled sleeves, e.g., in respective spools, grooves, and the like (not shown) on the roller 605. In this alternative, the collecting roller 605 may have a width similar to the source rollers 601, 602, e.g., such that collecting roller 605 may receive all of the sleeves made using the material from the source rollers 601, 602.

During use, at least two thin film sheets 601a, 602a are fed from the source rollers 601, 602, e.g., with their coated surfaces oriented towards one another. Alternatively, the coated surfaces may be oriented away from one another, e.g., if the resulting thin-walled sleeves are to be inverted similar to other embodiments described elsewhere herein. The sheets 601a, 602a may ride over the tensioning element 603 and through the cutting/sealing elements 604. With additional references to FIGS. 14C and 14D, as the thin film sheets 601a, 602a pass through the cutting/sealing elements 604, the sheets 601a, 602a may be cut into pairs of strips 601b, 602b that lie against or adjacent one another. In addition, the edges 607 of the pairs of strips 601b, 602b may be sealed together by the cutting/sealing elements 604 to substantially simultaneously form multiple thin-walled sleeves 606 having two longitudinal seams 607. The collecting roller(s) 605 may pick up the formed thin-walled sleeves 606 and store them for subsequent processing and/or use.

Figure 14C:
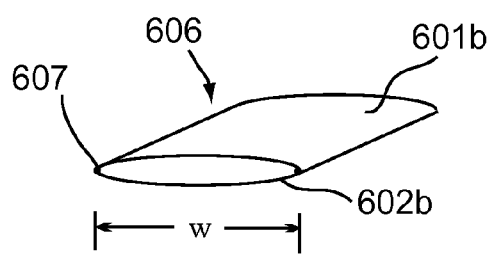
FIGS. 14C and 14D are cross-sectional views of an exemplary embodiment of a sleeve made using the apparatus and method of FIGS. 14A and 14B, with the sleeve collapsed and expanded, respectively.
Figure 14D:
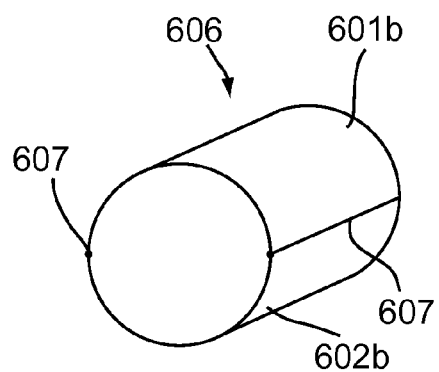

The thin-walled sleeves 606 may be collected in a substantially flat configuration onto the collecting roller(s) 605, such as that shown in FIG. 14C. In the flat configuration, the sleeves 606 are defined by the upper and lower strips 601b, 602b and the longitudinal seams 607. The width of the strips 601b, 602b corresponds substantially to the spacing of the cutting/sealing elements 604. The spacing of the cutting/sealing elements 604 may be adjustable, e.g., to allow the width of the strips 601b, 602b to be adjusted. The width "w" of the strips 601b, 602b may be substantially proportional to the diameter of the resulting thin-walled sleeves 606 when the sleeves 606 are expanded to a substantially circular configuration, such as that shown in FIG. 14D. Specifically, the width "w" may be defined substantially by the product w=π/2 d, where "w" is the width of the strip and "d" is the desired diameter of the thin-walled sleeves 606.

The width "W" of the sheets 601a, 601b (and hence the source rollers 601, 602) may be determined based upon the desired number of strips 601b, 601b and sleeves 606 to be formed from the sheets 601a, 601b. The optimal size of the sheets 601a, 601b may be selected based upon balancing efficiencies, e.g., between the complexities of handling and/or processing larger sheets and the increased productivity of simultaneously and continuously making more sleeves from individual sets of sheets. Generally, the width "W" of the sheets 601a, 601b may be determined by the product W=n w, where "n" is the desired number of sleeves to be formed from the sheets and "w" is the width of each of the resulting sleeves 606. It will be appreciated that these values may need to be adjusted depending upon waste and/or other processing factors. For example, if the strips 601b, 602b are bonded together using heat sealing, some of the width of the strips 601b, 602b may be lost to the longitudinal seams 607, although such adjustments may be easily determined.

Because of the continuous nature of the process, the entire lengths "L" of the sheets 601a, 602a may be formed into "n" long thin-walled sleeves 606 also having lengths "L." Subsequently, the long thin-walled sleeves 606 may be cut or otherwise formed into individual tubular devices, e.g., using a sheer or other mechanical cutting apparatus, laser cutting apparatus, and the like (not shown). If, however, the cutting process involves heat, the long thin-walled sleeve(s) 606 may be at least partially expanded before cutting to prevent the severed ends from bonding or otherwise becoming closed during cutting.

For example, each of the collecting rollers 605 may be fed or moved successively or simultaneously to a subsequent process step, which may involve sheering or otherwise cutting the long, substantially continuous sleeves 606 thereon into individual thin-walled sleeves or tubular devices (not shown) having desired lengths "l." Thus, each of the long thin-walled sleeves 606 may be formed into a desired number "m" individual tubular devices, where m<L/l, which may take into account any waste that may occur, e.g., between individual tubular devices and/or at the beginning and/or end of each of the long thin-walled sleeves 606.

The individual tubular devices may then provide or be incorporated into catheters, sheaths, or other final tubular devices, such as the apparatus described elsewhere herein. For example, one or more outer layers, e.g., optionally including a reinforcing layer and/or solid outer layer, may be provided around the individual thin-walled sleeves using any of the methods described elsewhere herein.

Alternatively, the entire length "L" of the thin-walled sleeves 606 from one or more collecting rollers 605 may be directed through another substantially continuous process, e.g., an extrusion and/or winding process (not shown), to provide one or more outer layers (also not shown) around the long thin-walled sleeves 606, e.g., using methods similar to the other embodiments described herein. The resulting structures may then be cut into individual tubular devices, and other components may be added, as desired. Thus, a pair of long sheets 601a, 602a may be formed into a total of m*n individual tubular devices without having to handle each of the individual tubular devices, which may improve efficiency, uniformity, and/or reduce cost compared to making individual tubular devices separately.

Turning to FIGS. 15A-15G, yet another apparatus 700 is shown for making thin-walled sleeves 706 or other tubular devices having coated surfaces, e.g., on one or more interior surfaces of the devices. Similar to the previous embodiments, the apparatus 700 includes one or more source rollers 701, and one or more cutting elements 704. The cutting elements 704 may be a plurality of blades, wires, or other cutters capable of slitting sheets of material, similar to the previous embodiments. Optionally, the apparatus 700 may also include one or more collecting rollers and/or drives (not shown), also similar to the previous embodiments.

In addition, the apparatus 700 includes a plurality of forming dies 708 for substantially continuously forming strips into sleeves 706, as described further below. Each forming die 708 includes a tapered housing 708a and a mandrel 708b disposed within the housing 708a. The housing 708a includes an enlarged inlet 708c oriented towards the cutting elements 7084 and a relatively narrow outlet 708d, which may be oriented towards the collecting roller(s) and/or other subsequent processing equipment (not shown). The mandrel 708b may have sufficient length to extend concentrically between and, optionally out of, the inlet 708c and/or outlet 708d and a diameter slightly smaller than the outlet 708d such that sleeves 706 may exit the housing 708a between the mandrel 708b and the outlet 708d. The mandrel 708b may be a rod, tube, or other forming element, e.g., formed from materials similar to the mandrels described elsewhere herein. The mandrel 708b and/or interior surfaces of the housing 708a may be formed from or coated with lubricious material to facilitate the strips 701b passing therethrough.

As shown in FIG. 15A, the source roller 701 includes a sheet 701a of source material wound thereon, e.g., after previous processing, such as extruding, coating one or more surfaces of the sheet 701a with one or more coatings, and the like, similar to the previous embodiments. The sheet 701a may be pulled off of the source roller 701, and directed successively through the cutting elements 704 and forming dies 708, e.g., by the collecting roller(s) and/or drives (not shown).

During use, the sheet 701a may be fed from the source roller 701 through the cutting elements 704, thereby cutting the sheet 701a into a plurality of substantially continuous strips 701b. The strips 701b may then be fed into respective forming dies 708 such that the strips 701*b* may be wound around the mandrels 708*b* as they pass through the housings 708*a*.

Snapshots of the process are illustrated in FIGS. 15C-15G, showing an exemplary strip 701*b* being wound around the mandrel 708*b* as the strip 701*b* passes through the housing 708*a*. As shown in FIG. 15B, the strip 701*b* includes a thin-walled film 701*b*-I having a coating 701*b*-ii thereon, and the coating 701*b*-ii is oriented towards the mandrel 708*b* as the strip 701*b* enters the housing 708*a*. As the strip 701*b* slides along the narrowing housing 708*a*, the strip 701*b* is directed around the mandrel 708*b*, e.g., until longitudinal edges of the strip 701 701*b* abut or are otherwise disposed adjacent one another.

Optionally, one or more components of the forming dies 708, e.g., the housing 708*a* and/or the mandrel 708*b*, may be heated to seal or reflow the material of the strips 701*b*, for example, to bond the longitudinal edges of the strips 701*b* to form longitudinal seam 701*c* and a substantially continuous tubular structure as shown in FIG. 15G. Alternatively localized heat, adhesive, ultrasonic energy may be applied to the abutted longitudinal edges of the strips 701*b* before exiting the outlet 708*d* of the housing 708*a* to create the longitudinal seam 701*c*. The apparatus 700 may be used to form substantially continuous thin-walled sleeves 706 from thin film sheets, which may be subsequently bonded to outer layers or otherwise processed to form tubular devices or other apparatus (not shown), similar to other embodiments described elsewhere herein. Alternatively, the apparatus 700 may be used to form structural tubular devices, e.g., from relatively thick sheets, similar to other embodiments described previously.

Figure 16A:
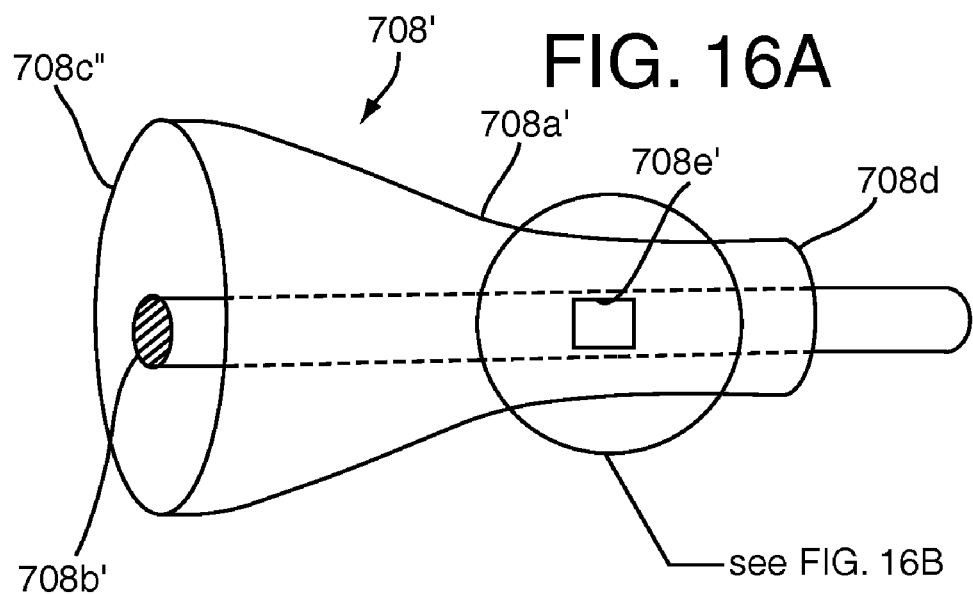
FIG. 16A is a side view of an alternative embodiment of a die including a window for applying heat to thin sheets as they pass through the die.
Figure 16B:
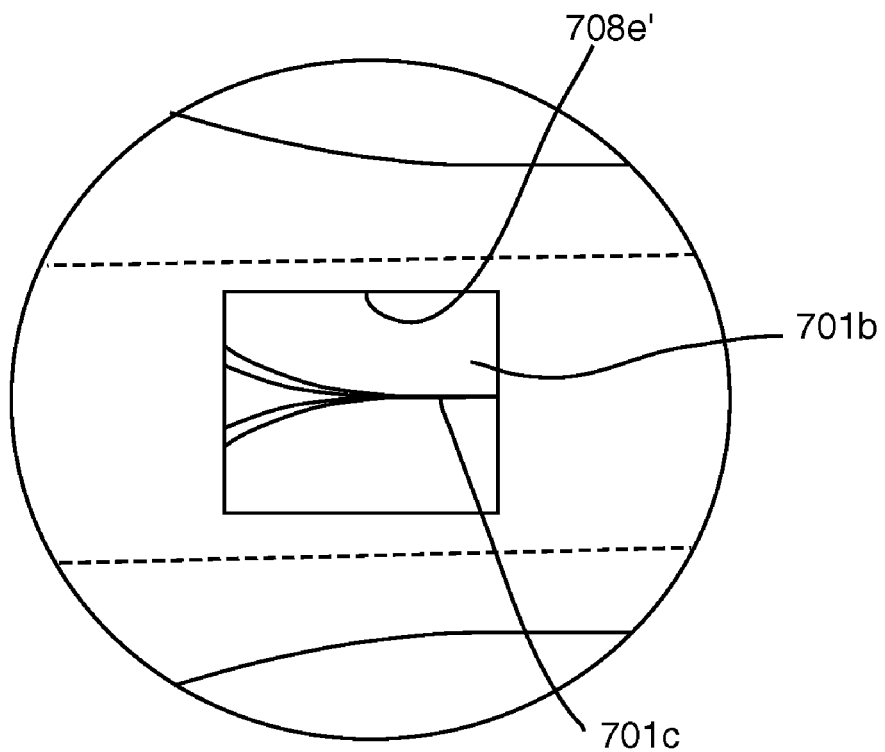
FIG. 16B is a detail of the die of FIG. 16A, showing a heat seal being formed along a thin sheet as it passes the window.

Alternatively, as shown in FIGS. 16A-16B, forming dies 708' may be provided that include a window 708*e*' in the housing 708*a*,' e.g., near or adjacent the outlet 708*d*' for creating a longitudinal seam 701*c* along longitudinal edges of the strip 701*b* passing therethrough. For example, the window 708*e*' may allow a bonding tool (not shown) to be inserted into the window 708*e*' to contact the strip 701*b* or otherwise provide local application of heat, ultrasonic energy, adhesive, solvent, or other method for seam creation. In addition, in the alternative shown in FIG. 16A, the mandrel 708*b*' of the forming die 708' may include a tapered shape, e.g., narrowing slightly from a first end at the inlet 708*c*' of the housing 708*a*' to a second end at the outlet 708*d*.' Such a tapered mandrel 708*b*' may be provided in the previous embodiment instead of the substantially uniform diameter mandrel 708 if desired to form the strip 701*b* into sleeves 706.

Figure 17:
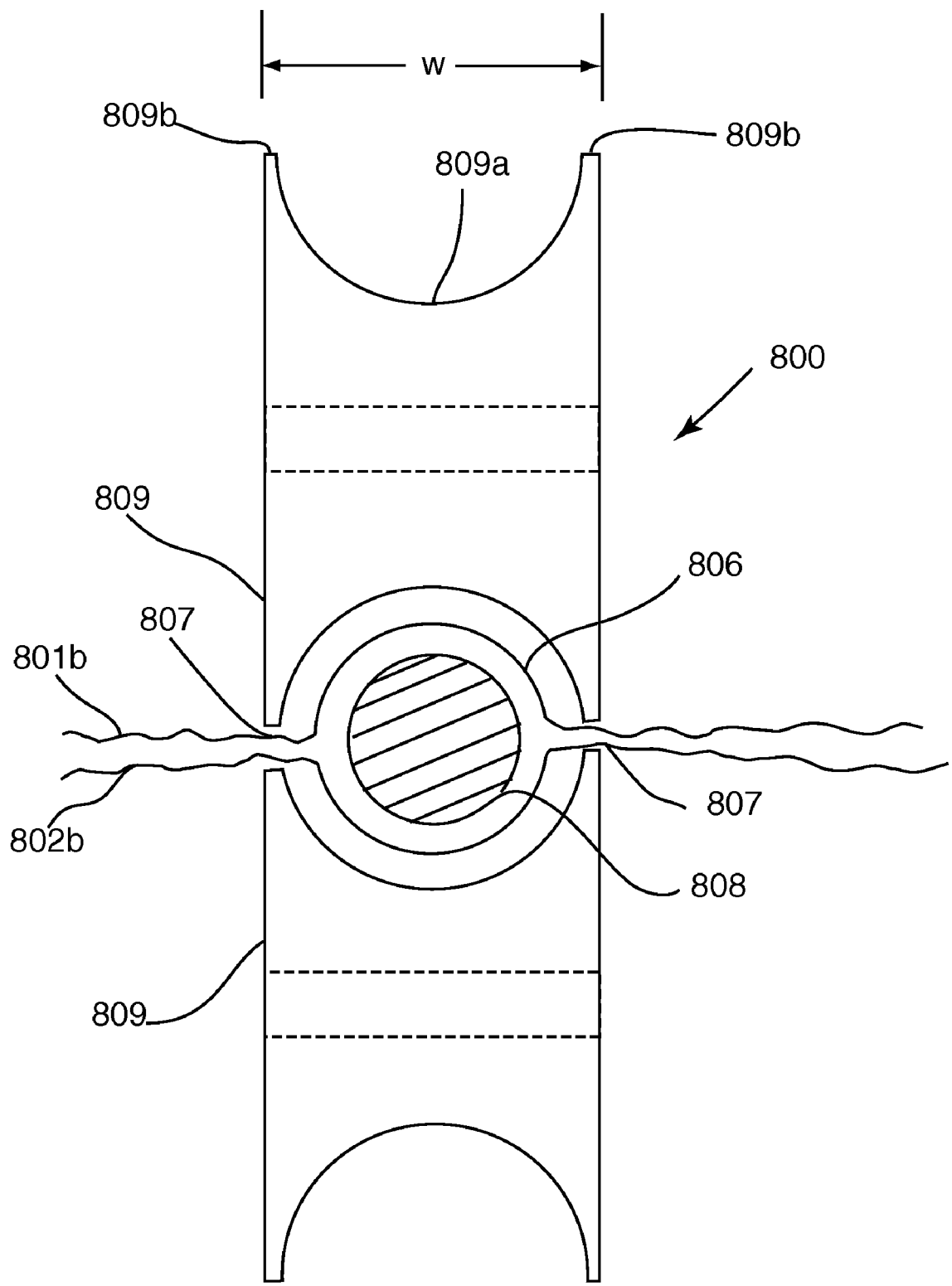
FIG. 17 is a cross-sectional view of another embodiment, showing an apparatus and method for making thin-walled sleeves.

Turning to FIG. 17, yet another apparatus 800 is shown for making multiple thin-walled sleeves simultaneously by substantially continuous process. Generally, the apparatus 800 may include components similar to the previous embodiments, e.g., one or more source rollers for carrying sheets (not shown), one or more cutting elements for separating the sheets into elongate strips (also not shown), and mandrels 808 for forming the strips into thin-walled sleeves. Optionally, the apparatus 800 may include one or more collecting rollers (not shown) for picking up the sleeves for subsequent processing, one or more motors or other drives, and/or other equipment in line with the mandrels 808 for further processing the sleeves, e.g., for providing outer layers and the like (not shown), similar to other embodiments described elsewhere herein.

Unlike the previous embodiments, the apparatus 800 includes pairs of forming rollers 809 disposed around mandrels 808 (with one mandrel 808 and one pair of rollers 809 being shown in FIG. 17 for illustrative purposes). The rollers 809 may include grooves 809*a* between rims 809*b* to accommodate receiving a mandrel 808 between each pair of rollers 809. The width "w" of the rims 809*b* may correspond to the desired diameter of the sleeves to be formed, e.g., based upon the product of w=π/2 d, where "d" is the desired diameter for the sleeves. The depth of the grooves 809*a* may be sufficient to receive the mandrels 808 between the rollers 809 with sufficient space to pass sheet material between the mandrels 808 and rollers 809 with minimal clearance, e.g., to prevent excess material from being receive between the mandrels 808 and rollers 809. The mandrels 808 and/or rollers 809 may be made from any suitable material similar to the other embodiments described herein, such as copper, PTFE, acetal, and the like, e.g., including lubricious coatings if desired.

In one embodiment, the apparatus 800 may include a pair of source rollers carrying thin sheets having a coating on first surfaces that are disposed adjacent one another when the sheets are fed from the source rollers (not shown), e.g., similar to the embodiment shown in FIGS. 14A and 14B. The sheets may be fed through one or more cutting elements, e.g., also similar to the embodiments shown in FIGS. 14A and 14B, to separate the sheets into a plurality of pairs of strips 801*b*, 802*b*. However, the pairs of strips 801*b*, 802*b* may remain separated from one another or may be bonded together after being directed through the cutting element(s). In addition, the spacing of the cutting elements may be greater than the width "w" of the rims 809*b* of the rollers 809, e.g., such that the width of the strips 801*b*, 802*b* is also greater than the width "w" of the rims 809*b*.

Each of the pairs of strips 801*b*, 802*b* may then be directed over a respective mandrel 808 and between the respective pair of rollers 809, as shown in FIG. 17. The rollers 809 may be spaced apart sufficiently from one another such that the rollers 809 contact the strips 801*b*, 802*b* between the mandrel 808 and the longitudinal edges of the strips 801*b*, 802*b*. The rollers 809 may be heated to bond the strips 801*b*, 802*b* to one another, thereby creating longitudinal seams 807. Optionally, thereafter, the excess material 810*a*, 810*b* between the longitudinal seams 807 and the outer longitudinal edges may be cut off or otherwise removed to provide substantially continuous thin-walled sleeves 806. Thereafter, the sleeves 806 may be subjected to winding onto collecting roller(s) (not shown), and/or further processing, for example, coextrusion, reflowing, and the like, to incorporate the thin-walled sleeves 806 as liners for lumens of tubular devices as previously described, and/or to cut the sleeves into individual lengths, also as described previously.

Alternatively, the thin film sheets 801*b*, 802*b* may be cut and sealed substantially simultaneously by the rims 809*b* of the rollers 809, e.g., by sharpening the rims 809*b*, heating the rollers 809, and the like such that separate cutting elements are not necessary. In a further alternative, the cutting elements may be sharpened rollers (not shown) disposed immediately adjacent rollers 809. In another alternative, the sheets 801*b*, 802*b* may be fed over the mandrel 808 and through the rollers 809 to create the longitudinal seams 807 before cutting or otherwise separating the sheets 801*b*, 802*b* into separate sleeves 806. After the longitudinal seams 807 are created, the bonded sheets 801*b*, 802*b* may be fed through a cutting apparatus, similar to those described elsewhere herein, to separate the bonded sheets 801*b*, 802*b* into separate sleeves 806, e.g., removing any excess material between adjacent sleeves simultaneously with, before, or after creating the separate sleeves 806.

Figure 23A:
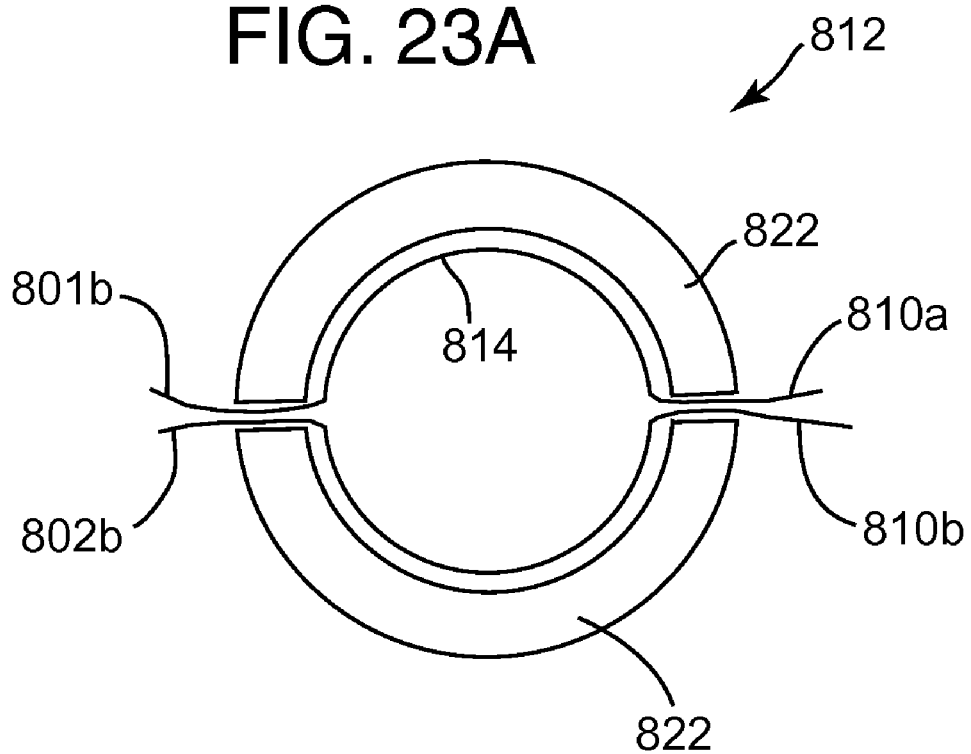
FIGS. 23A and 23B are cross-sectional views of a tubular apparatus being formed that includes an inner liner made using the apparatus and methods described herein.
Figure 23B:
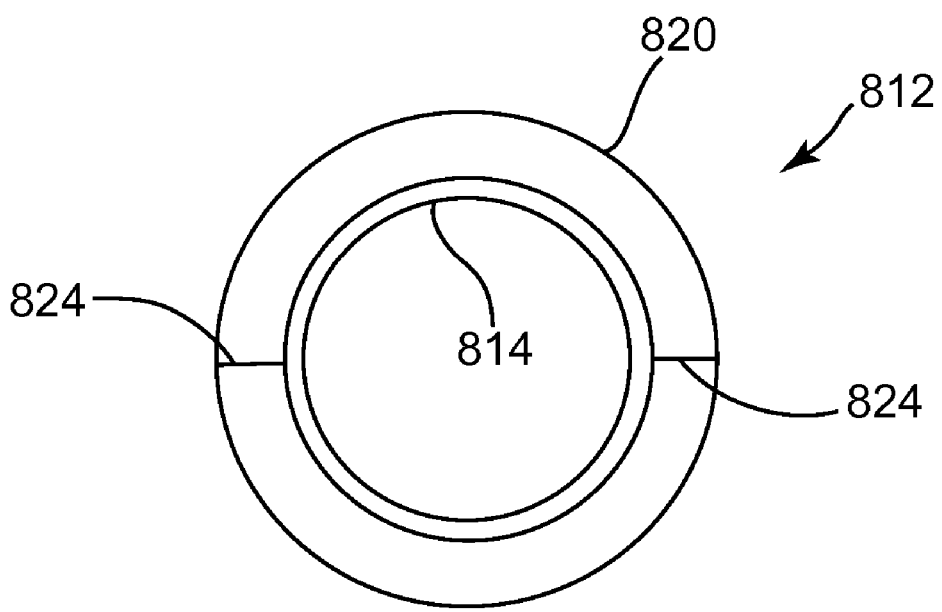

In yet another alternative, one or both excess edges of the sleeves 806 may remain until after further processing. For example, a tubular structure (not shown) may be bonded or otherwise attached around one of the sleeves 806 (either before or after separating the sleeve 806 into individual tubular devices). For example, as shown in FIGS. 23A and 23B, a tubular structure 820 may be formed or split into two halves 822, which may then be attached around the sleeve 806, e.g., such that the excess material 810a, 810b extends out from between the halves 822, similar to other embodiments described herein. The excess material 810a, 810b outside the tubular structure 820 may be cut off or otherwise removed.

Figure 18:
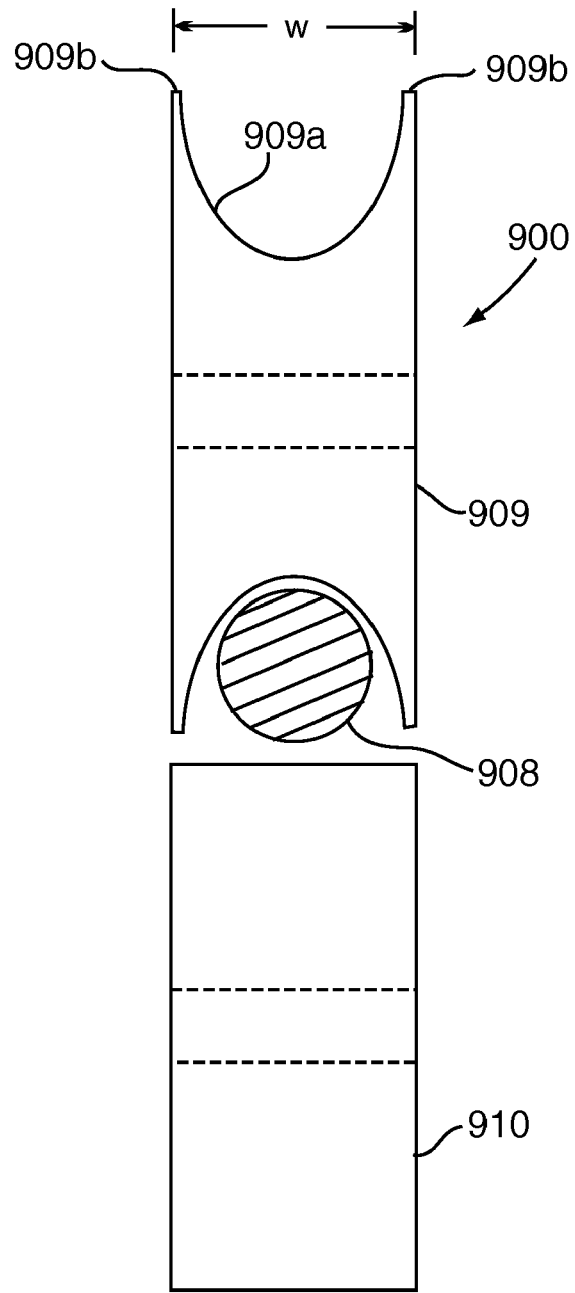
FIG. 18 is a cross-sectional view of yet another embodiment, showing an apparatus and method for making thin-walled sleeves.

Turning to FIG. 18, an alternative embodiment of an apparatus 900 is shown for making multiple thin-walled sleeves substantially simultaneously by continuous process. The apparatus 900 is generally similar to the embodiment of FIG. 17, e.g., including a mandrel 908, and a pair of rollers 909, 910, wherein a thin-walled sleeve (not shown) is formed over the mandrel 908. Unlike the previous embodiment, only the first roller 909 includes a groove 909a defined by rims 909b adapted to provide sufficient space to accommodate the mandrel 908 therein. The second roller 910 includes a substantially flat outer circumference, i.e., without a groove. The apparatus 900 may be used to make thin-walled sleeves from two thin film sheets (not shown) otherwise similar to the embodiment shown in FIG. 17. The first and second rollers 909, 910 are sufficiently spaced to accommodate receiving the strips (or sheets) therebetween the mandrel 908 and the rollers 909, 910, with the rims 909b creating longitudinal seams as the strips (or sheets) pass between the mandrel 908 and the rollers 909, 910.

Figure 19A:
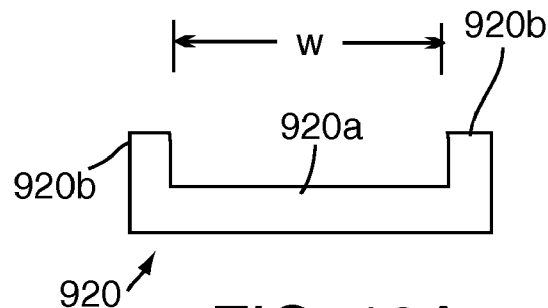
FIGS. 19A and 19B are cross-sectional views of film sheets that may be fed through an apparatus, such as those of FIGS. 17 and 18 for making thin-walled sleeves.

Turning to FIG. 19A, which is not drawn to scale, a cross section of an exemplary embodiment of a thin film sheet or strip 920 is shown. The strip 920 includes a relatively thin main region 920a disposed between ridges 920b. The main region 920a may have a width "w," e.g., that may be the same or wider than the width "w" of the rims 909b of the roller 909 (or other cutting and/or sealing elements, such as those described elsewhere herein). The main region 920a may also include a coating on at least one surface thereof, similar to other embodiments described herein. The ridges 920b may facilitate feeding the strip 920 through a forming apparatus (not shown), such as those having rollers as previously described. For example, the rollers may include outer hubs that may contact the ridges 920b, such that the contact between the hubs and ridges 920b are used to direct the strip 920 through the forming apparatus with reduced risk of tearing, binding, and the like. Alternatively, the ridges 920b may be received in a groove or other track (not shown) in the rollers to keep the main region 920a aligned within rims of the rollers and/or around a mandrel (also not shown), similar to the previous embodiments.

Figure 19B:
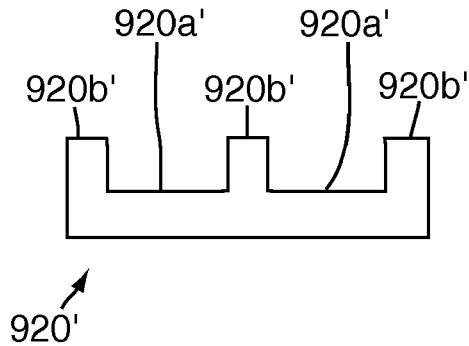

The ridges 920b may be formed at the time of extruding or other forming of the sheet material for the strip 920. For example, as shown in FIG. 19B, a sheet 920' may be formed including a plurality of relatively thin main regions 920a' separated by ridges 920b' (with two exemplary main regions 920a' and three ridges 920b' shown for simplicity). The sheet 920' may be extruded or otherwise formed substantially continuously, and used in any of the apparatus and methods described herein. Optionally, one or more coatings may be applied to the sheet 920,' e.g., to the main regions 920a' between the ridges 920b,' or to the entireties of one or both sides of the sheet 920.' During use, the sheet 920' may be cut or otherwise separated into long strips, e.g., by cutting through the ridges 920b,' e.g., to provide strips similar to the strip 920 shown in FIG. 19. After forming the strip (or strips) 920 into sleeves, the ridges may be disposed outside the longitudinal seams, and may be cut off or otherwise removed, similar to previous embodiments.

Figure 20:
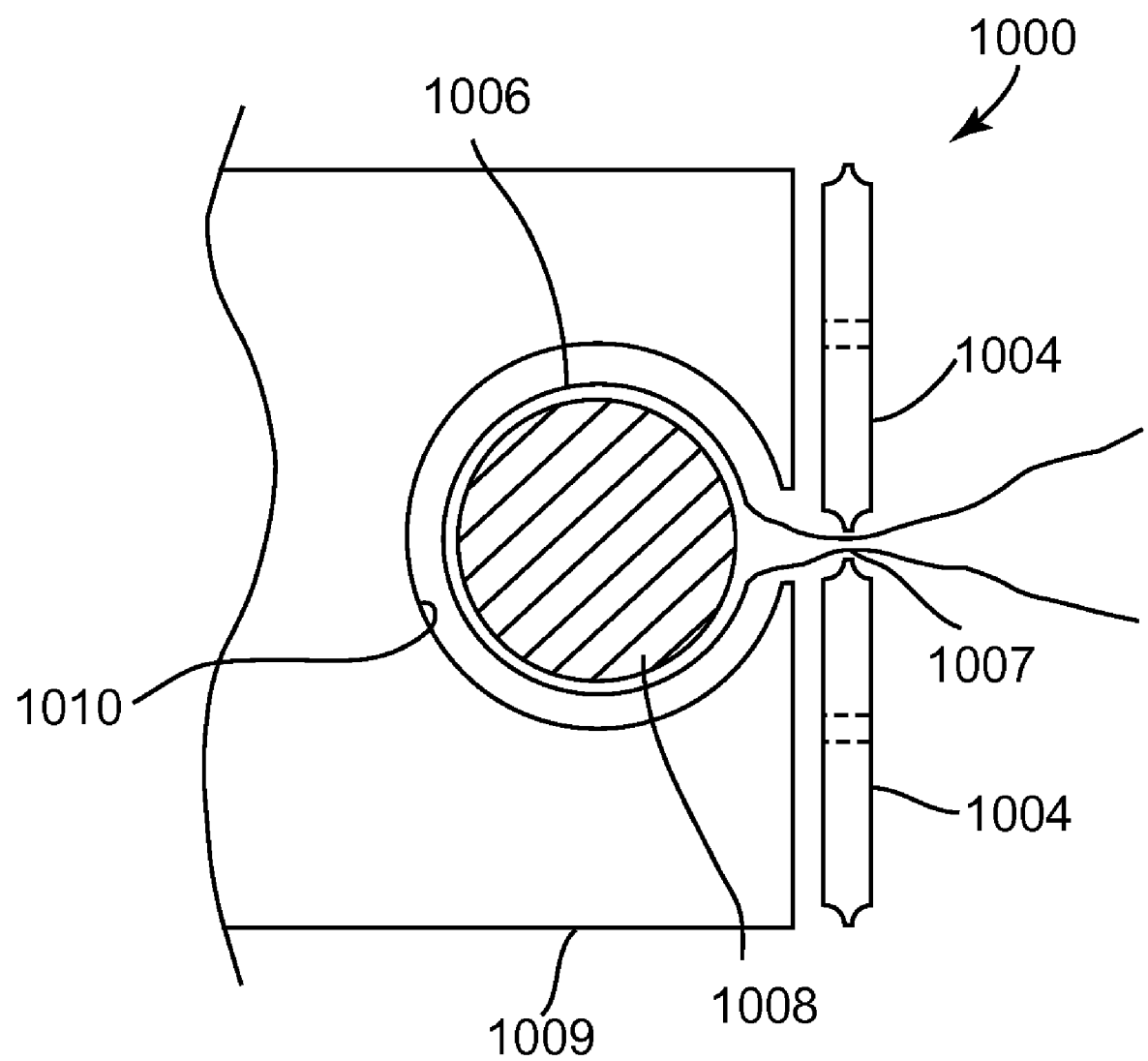
FIG. 20 is a cross-sectional view of still another embodiment of apparatus for making thin-walled sleeves using a substantially continuous process.

Turning to FIG. 20, yet another apparatus 1000 is shown for making one or more thin-walled sleeves 1006 by substan-tially continuous process. As shown, the apparatus 1000 includes a die 2001 including a channel or space 1010 within which a mandrel 1008 is disposed. The mandrel 1008 and channel 1010 are sized such that a thin film sheet 1006 may be received therebetween. The apparatus 1000 also includes a sealing element 1004 for creating a longitudinal seam 1007 substantially continuously along the sheet 1006. For example, as shown, the cutting element includes two opposing rollers 1004, which may be spaced slightly apart from one another to receive longitudinal edges of the sheet 1006 that extend from the channel 1010 between the rollers 1004. The rollers 1004 may be heated to bond the longitudinal edges and form the longitudinal seam 1007 as the sheet 1006 passes between the rollers 1004.

Alternatively, the sealing element 1004 may include other elements, e.g., pins, blades, applicators, and the like (not shown), which may create the longitudinal seam 1007 by ultrasonic welding, heating or other fusing, applying an adhesive, and the like. Optionally, the sealing element 1004 may also cut or otherwise remove the excess material substantially simultaneously with creating the longitudinal seam 1007. Alternatively, a cutting element (not shown) may be provided, e.g., after the sealing element 1004 to remove the excess material.

During use, the apparatus 1000 may be used to form one or more long thin-walled sleeves, similar to the previous embodiments. For example, the apparatus 1000 may be used in the process described in conjunction with FIG. 15A, except that the apparatus 1000 may replace each of the forming dies 708. Thus, a sheet may be separated into multiple strips, which may be directed into respective dies 1009. Each individual strip 1006 may be fed into the channel 1010 of the respective die 1009 and around the respective mandrel 1008 in a substantially continuous fashion. As the strip 1006 passes between the sealing elements 1004, the strip 1006 may be formed into a long thin-walled sleeve, by forming longitudinal seam 1007. The resulting sleeve may collected, further processed, and/or cut into individual tubular devices, similar to the previous embodiments.

Figure 21:
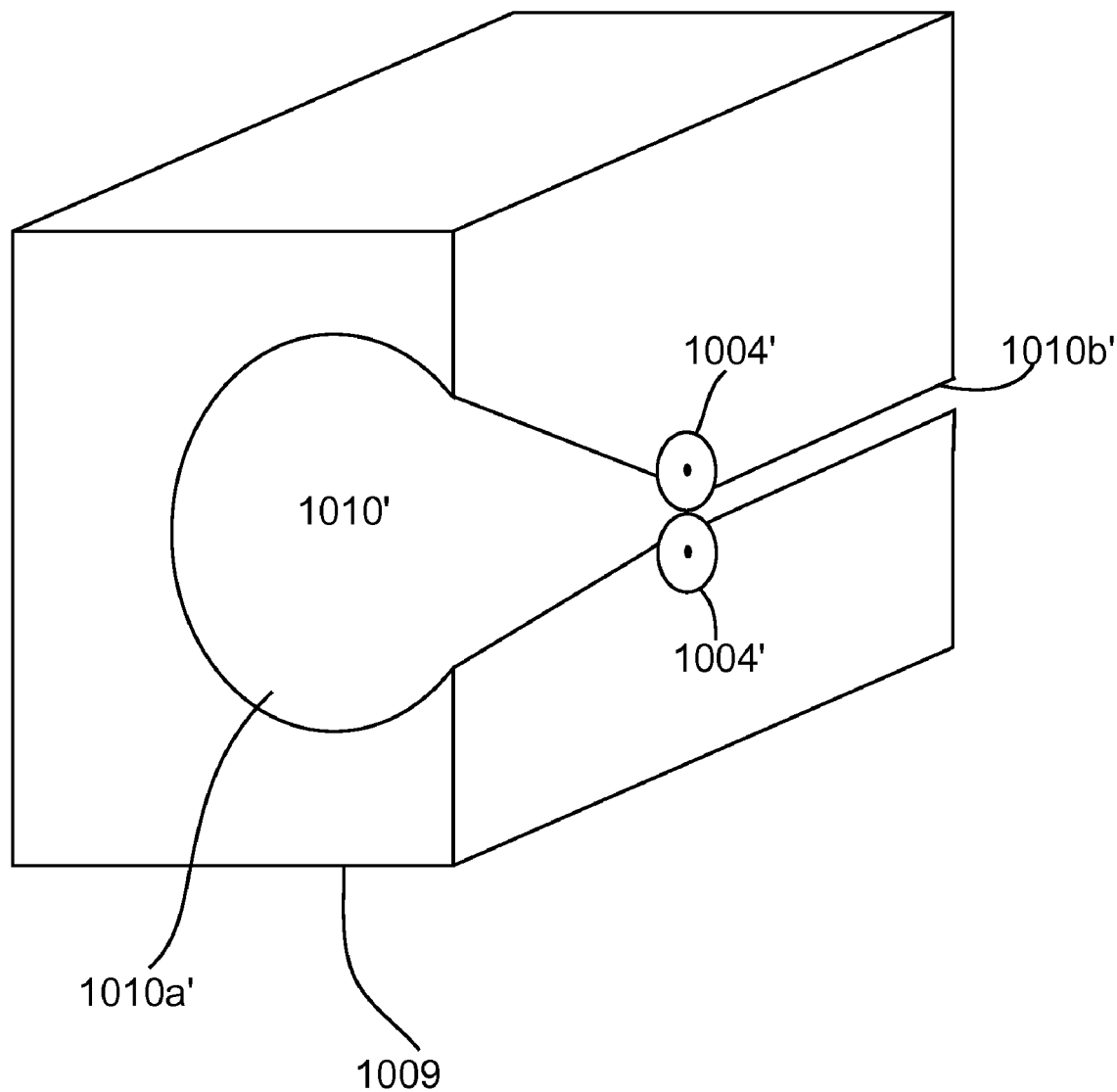
FIG. 21 is a perspective view of an alternative embodiment of the apparatus of FIG. 20.

FIG. 21 illustrates an alternative embodiment of a die 1009,' which may be made and/or used similar to the die 1009 described in conjunction with FIG. 20. Unlike the previous embodiment, the die 1009' includes a channel 1010' that includes a relatively wide inlet 1010a' that tapers to a relatively narrow outlet 1010b The die 1009' may include one or more sealing elements 1004,' e.g., one or more rollers, wires, blades, and the like, that may be used to create a longitudinal seam as a thin film sheet (not shown) is fed through the channel 1010' in the die 1009.' For example, the die 1009' may be heated at the point of the narrowing, or the sealing element(s) 1004' may be positioned at the narrowing or may themselves form the narrowing and perform sealing. The wide inlet 1010a' may facilitate guiding a sheet into the die 1009,' e.g., similar to the tapered housing in the forming die shown in FIGS. 15A and 15B. Otherwise, the die 1009' may be used similar to the previous embodiments described herein.

Figure 22A:
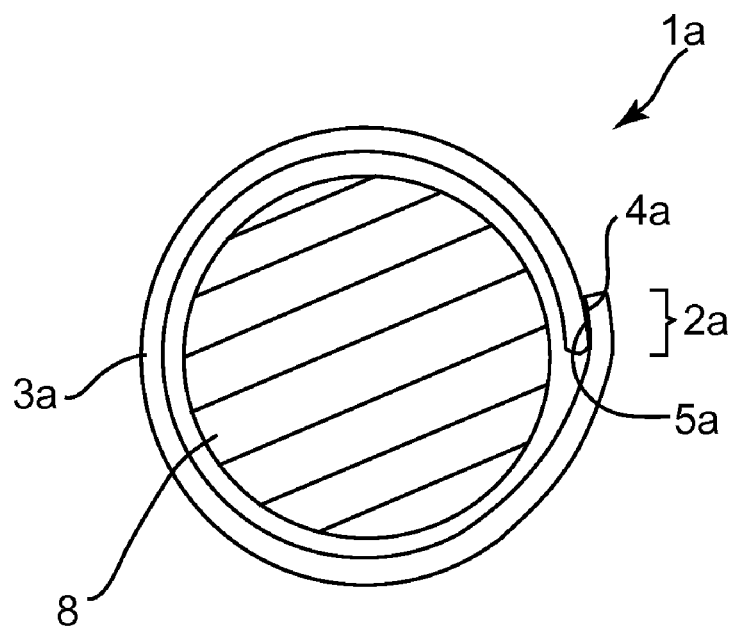
FIGS. 22A and 22B are cross-sectional views of alternate configurations for seams that may be formed on thin-walled sleeves using the apparatus and methods described herein.
Figure 22B:
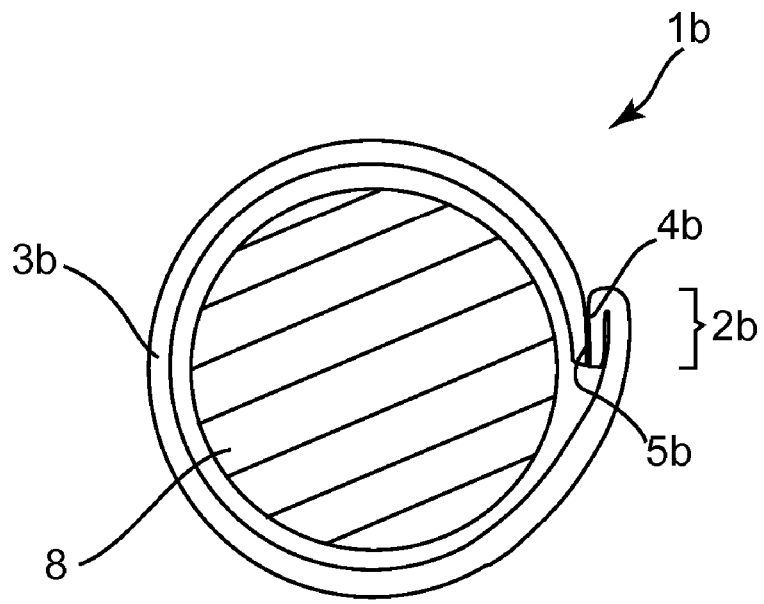

Turning to FIGS. 22A and 22B, exemplary embodiments of thin-walled sleeves 1 are shown that may include lapped longitudinal seams 2, which may be provided in any of the embodiments described herein, e.g., instead of butted seams. The thin-walled sleeves 1 may be formed from one or more coated thin membrane sheets, such as any of the strips or sheets described above. It will be appreciated that these drawings are not to scale, as the sleeves 1 may have relatively thin walls, e.g., having a thickness not more than 0.01 inch (0.25 mm), compared to the diameter of the mandrels 8 involved.

Such seams 2 may be used to dispose a coated surface interiorly while using one or more uncoated surfaces to form the seams 2. For example, as shown in FIG. 22A, a thin membrane sheet 3a may be wrapped around a mandrel 8 and edges overlapped, e.g., such that a longitudinal seam 2a is formed between one outer surface region 4a and one inner surface region 5a. In this embodiment, the inner surface of the sheet 3a may be coated except for the inner surface region 5a used to create the seam 2a. Alternatively, the inner surface region 5a may also be coated as long as the coating is compatible with the method used for bonding the inner and outer surface regions 5a, 4a together. Alternatively, as shown in FIG. 22B, the sleeve 1b may include a longitudinal seam 2b that may be formed between two outer surface regions 4b, 5b. In this alternative, the seam 2b may be unaffected by any coating on the inner surface since only uncoated outer surface regions 4a, 5b are bonded together.

Turning to FIGS. 23A and 23B, an exemplary embodiment of a tubular apparatus 812 is shown, which may be generally similar to other embodiments described previously, such as the apparatus shown in FIG. 1. The tubular apparatus 812 generally includes an inner liner 814 formed from a thin-walled sleeve, e.g., a length of sleeve 806 shown in FIG. 17, and an outer layer 820. As shown, the inner liner 814 may be formed from two thin membrane sheets 801b, 802b, e.g., having a coated surface disposed inwardly wherein the coating applied to the surface decreases the bondability of the surface. The tubular apparatus 812 may be formed by heating and reflowing the thin membrane sheets 801b, 802b and outer layer 820, leaving a layer of excess membrane material 810a, 810b extending through the wall of the outer layer 2302. This material may create a bonded seam 824 that is weaker than the adjacent material, e.g., to provide a preferential tearing seam. This weakened seam 824 may be used to facilitate slitting, splitting, or peeling away of the tubular apparatus 810 in the course of a procedure, e.g., as described elsewhere herein. It may be appreciated that a single or multiple longitudinal weaknesses may be created in a similar manner, e.g., using the other apparatus and methods described herein. Optionally, a thread or other structure (not shown) may be applied between or embedded within one of the sheets 801a, 801b, which may be pulled from one end of the tubular apparatus 812 to cause the seam 824 to separate, e.g., after introducing the tubular apparatus 812 into a patient's body during a procedure.

It will be appreciated that elements or components shown with any embodiment herein are exemplary for the specific embodiment and may be used on or in combination with other embodiments disclosed herein. For example, in the substantially continuous processes described herein, it may be possible to roll a thin-walled sheet without bonding the longitudinal edges, and insert the rolled thin-walled sheet into a subsequent process, e.g., providing a reinforcing layer, tubular structure, and the like, around the rolled sheet, e.g., in a substantially continuous process. Optionally, the sheet and/or any surrounding layers may be heated to bond the layers together or otherwise form a desired tubular device, which may also be completed substantially continuously.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

We claim:
1. A method for making a plurality of tubular devices sized for introduction into a body lumen, comprising:
providing first and second sheets adjacent one another such that first surfaces of the sheets are oriented towards one another and second surfaces of the sheets are oriented away from one another;
directing the first and second sheets through a cutting apparatus such that the first and second sheets are cut into multiple pairs of strips; and
bonding the pairs of strips together to create a plurality of thin-walled sleeves having inner lumens defined by the first surfaces,
wherein the first surfaces of the first and second sheets comprise a hydrophilic coating.
2. The method of claim 1, wherein the pairs of strips are bonded together when the first and second sheets are directed through the cutting element.
3. The method of claim 1, wherein providing the first and second sheets comprises providing rolls including the first and second sheets wound around the rolls such that the sheets may be fed substantially continuously through the cutting element.
4. The method of claim 1, further comprising cutting the thin-walled sleeves into individual lengths.
5. A method for making a plurality of tubular devices sized for introduction into a body lumen, comprising:
providing first and second sheets adjacent one another such that first surfaces of the sheets are oriented towards one another and second surfaces of the sheets are oriented away from one another;
directing the first and second sheets through a cutting apparatus such that the first and second sheets are cut into multiple pairs of strips; and
bonding the pairs of strips together to create a plurality of thin-walled sleeves having inner lumens defined by the first surfaces;
cutting the thin-walled sleeves into individual lengths; and
attaching a tubular structure around each of the individual lengths of the thin-walled sleeves.
6. The method of claim 4, wherein the tubular structure comprises a reinforcement layer and an outer continuous layer.
7. A method for making a plurality of tubular devices sized for introduction into a body lumen, comprising:
providing first and second sheets adjacent one another such that first surfaces of the sheets are oriented towards one another and second surfaces of the sheets are oriented away from one another;
directing the first and second sheets through a cutting apparatus such that the first and second sheets are cut into multiple pairs of strips; and
bonding the pairs of strips together to create a plurality of thin-walled sleeves having inner lumens defined by the first surfaces,
wherein the first and second sheets comprise polyurethane.
8. The method of claim 1, further comprising winding the thin-walled sleeves around one or more collecting rollers.
9. The method of claim 1, wherein the cutting element maintains sufficient tension on the first and second sheets to maintain the first and second sheets in contact with one another when the first and second sheets are cut and bonded.
10. The method of claim 1, wherein the cutting element comprises a heated element that bonds longitudinal edges of the pairs of strips substantially simultaneously with cutting the first and second sheets.

11. A method for making a plurality of tubular devices sized for introduction into a body lumen, comprising:
  providing first and second sheets adjacent one another such that first surfaces of the sheets are oriented towards one another and second surfaces of the sheets are oriented away from one another;
  directing the first and second sheets through a cutting apparatus such that the first and second sheets are cut into multiple pairs of strips; and
  bonding the pairs of strips together to create a plurality of thin-walled sleeves having inner lumens defined by the first surfaces,
  wherein the pairs of strips are bonded together by directing the pairs of strips between respective mandrels and pairs of rollers.

12. The method of claim 11, wherein the pairs of rollers create longitudinal seams substantially continuously as the pairs of strips are directed through the respective mandrels and pairs of rollers.

13. A method for making a plurality of tubular devices sized for introduction into a body lumen, comprising:
  providing a first sheet having first and second surfaces, the first surface comprise a coating having one or more desired properties;
  feeding the first sheet through a cutting tool to separate the first sheet into a plurality of elongate strips;
  forming the strips into elongate sleeves such that the first surface defines a lumen within the sleeves;
  cutting each of the sleeves into individual tubular devices; and
  attaching a tubular structure around each of the individual tubular devices to create a catheter.

14. The method of claim 13, wherein the strips are formed into elongate sleeves by feeding the strips through respective forming dies.

15. The method of claim 14, wherein each of the forming dies comprises a housing surrounding a mandrel, the housing tapered around the mandrel such that, as a strip is fed through the housing, the strip is formed into a tubular sleeve.

16. A method for making a plurality of tubular devices sized for introduction into a body lumen, comprising:
  providing a first sheet having first and second surfaces, the first surface comprise a coating having one or more desired properties;
  feeding the first sheet through a cutting tool to separate the first sheet into a plurality of elongate strips;
  forming the strips into elongate sleeves such that the first surface defines a lumen within the sleeves; and
  cutting each of the sleeves into individual tubular devices,
  wherein the strips are formed into elongate sleeves by feeding the strips through respective forming dies,
  wherein each of the forming dies comprises a housing surrounding a mandrel, the housing tapered around the mandrel such that, as a strip is fed through the housing, the strip is formed into a tubular sleeve, and
  wherein at least a portion of each forming die is heated to bond longitudinal edges of the strip fed through the housing together to form the tubular sleeve.

17. The method of claim 15, wherein a heating element is applied to the strip as the strip is fed through the housing to bond longitudinal edges of the strip fed through the housing together to form the tubular sleeve.

18. The method of claim 14, wherein the strips are fed through channels in the respective forming dies such that longitudinal edges of the strips extend out of the channels, and wherein longitudinal seams are created along the strips as they pass through the channels.

19. The method of claim 18, wherein the forming dies comprise one or more sealing elements that create the longitudinal seams as the strips pass the one or more sealing elements.

20. A method for making a plurality of catheters sized for introduction into a body lumen of a patient, comprising:
  providing a first sheet having first and second surfaces, the first surface comprise a coating having one or more desired properties;
  feeding the first sheet through a cutting tool to separate the first sheet into a plurality of elongate strips, each strip having first and second side edges;
  thereafter, rolling each of the strips such that the first and second side edges are disposed adjacent one another and the coated first surface is disposed inwardly and the second surface of the sheet is disposed outwardly;
  cutting each of the rolled strips into individual tubular devices; and
  attaching a tubular structure around each of the individual tubular devices to create a catheter sized for introduction into a body lumen of a patient.

21. The method of claim 20, wherein attaching a tubular structure around each of the individual tubular devices heating at least one of the tubular structure and each of the individual tubular devices to bond the second surface of the sheet to the tubular structure.

22. The method of claim 21, wherein the sheet comprises thermoplastic material, and wherein heating causes the thermoplastic material of the sheet to reflow and bond to the tubular structure.

23. The method of claim 20, further comprising creating a longitudinal seam along the first and second side edges of each of the individual tubular devices to create a sleeve before attaching the tubular structure around each of the individual tubular devices.

24. The method of claim 20, wherein the coating comprises a hydrophilic coating.

* * * * *